Figure 2:
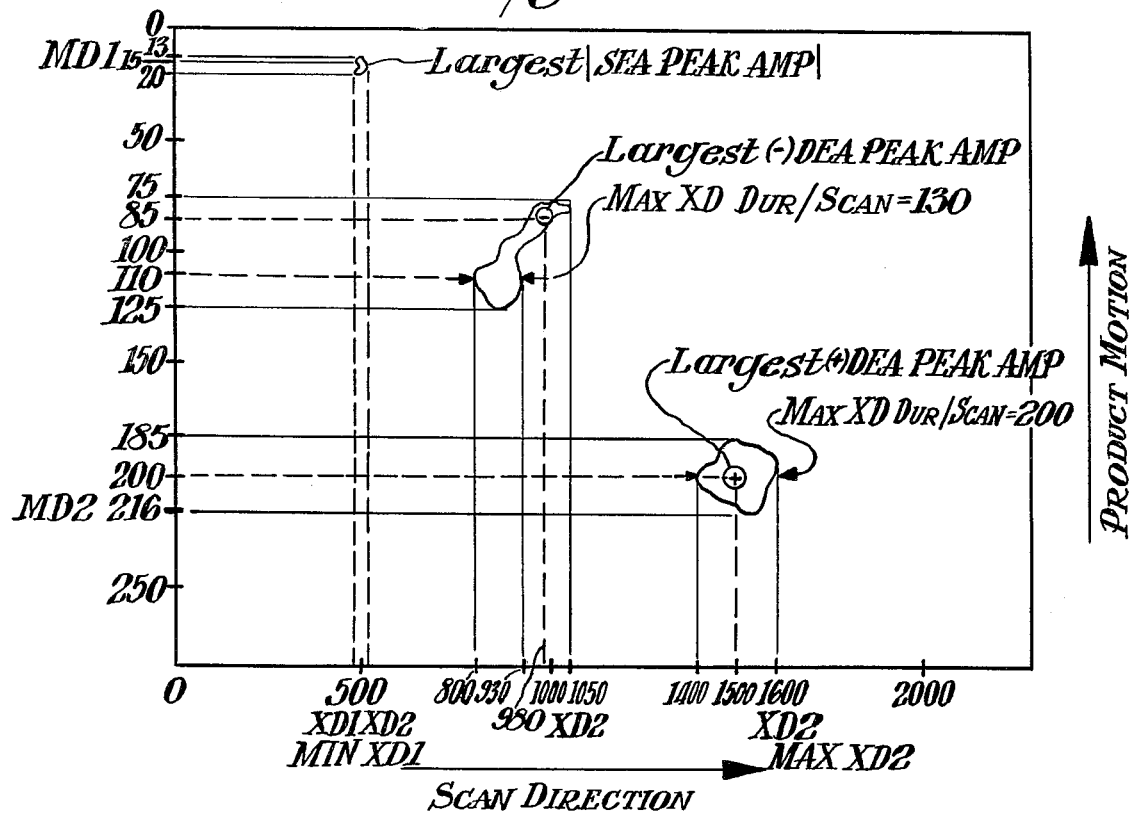

United States Patent [19]
Piovoso et al.

[11] 4,237,539
[45] Dec. 2, 1980

[54] ON-LINE WEB INSPECTION SYSTEM

[75] Inventors: Michael J. Piovoso, Newark; Edmund H. Smith, Jr., Wilmington; William E. Wolf, Newark, all of Del.

[73] Assignee: E. I. Du Pont de Nemours and Company, Wilmington, Del.

[21] Appl. No.: 853,421

[22] Filed: Nov. 21, 1977

[51] Int. Cl.$^3$ .................. G01N 21/84; G06F 15/20
[52] U.S. Cl. .................. 364/552; 250/562; 356/430; 364/507
[58] Field of Search .............. 364/507, 552, 571, 580; 250/559, 562, 563, 571, 572; 73/1 R, 88 R; 356/237, 238, 199, 200, 429, 430; 340/213 R, 213 Q, 259, 260, 146.3 AC; 209/111.5

[56] References Cited

U.S. PATENT DOCUMENTS

| | | | |
|---|---|---|---|
| 3,280,692 | 10/1966 | Milnes et al. | 356/158 |
| 3,359,853 | 12/1967 | Benson et al. | 356/201 |
| 3,389,789 | 6/1968 | Watson et al. | |
| 3,410,643 | 11/1968 | Jörgensen | 364/507 |
| 3,524,988 | 8/1970 | Gaither | 250/219 |
| 3,534,402 | 10/1970 | Crowell et al. | 364/552 |
| 3,545,610 | 12/1970 | Kelly et al. | 209/73 |
| 3,581,888 | 6/1971 | Kelly et al. | 209/75 |
| 3,636,513 | 1/1972 | Tisdale | 340/146.3 AC |
| 3,638,188 | 1/1972 | Pincoffs et al. | 340/146.3 AC |
| 3,747,755 | 7/1973 | Senturia et al. | 209/111.5 |
| 3,781,117 | 12/1973 | Laycak et al. | 356/237 |
| 3,781,531 | 12/1973 | Baker | 364/507 |
| 3,803,420 | 4/1974 | Bossons | 250/562 |
| 3,859,537 | 1/1975 | Wolf | 250/559 |
| 3,878,384 | 4/1975 | Bowker | 364/570 |
| 3,900,265 | 8/1975 | Merlen et al. | 364/552 |
| 3,917,414 | 11/1975 | Geis et al. | 356/200 |
| 3,983,375 | 9/1976 | Johnson | 364/552 |
| 4,051,722 | 10/1977 | Feller | 364/552 |

FOREIGN PATENT DOCUMENTS 1409653 10/1975 United Kingdom.

*Primary Examiner*—Errol A. Krass

[57] ABSTRACT

An automatic on-line computer-aided inspection system for a running web utilizing a transverse web scanning means, detection means incorporating feature extraction and processing circuitry for generating unique output signals corresponding to said web scanning characteristic of web features of inspection interest, means converting the output signals to digital data words input sequentially to a digital computer, said computer applying one or more algorithms to said words, thereby calibrating the values of said features of said words, comparing said calibrated feature values to at least one set of product-qualifying values held in memory, and means responsive to the computer classifying the web as acceptable or non-acceptable as regards areas of preselected marketable size in the web.

7 Claims, 14 Drawing Figures

| DEFECT | DESCRIPTION | TYPICAL WAVEFORM |
|---|---|---|
| BASE DIRT | SHARPLY DEFINED SPECK ABOUT 1MM DIAMETER. SEEN IN TRANSMISSION (T) MODE ONLY. A "NO-GO" DEFECT. | 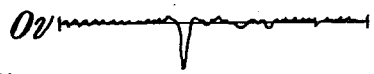 Time → |
| BASE DYE 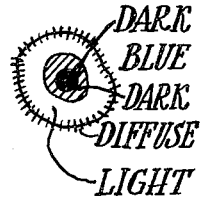 | A DARK BLUE DYE GRANULE 1-5 MM IN DIAMETER IMMEDIATELY SURROUNDED BY A DARK FIELD, THEN A LIGHTLY SHADED FIELD WITH DIFFUSE EDGES ~.25-1.0 CM IN DIAMETER SEEN IN TRANSMISSION ONLY. A "GO" DEFECT. | 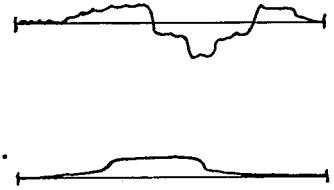 |
| RESIN PICKOFF | A MILDLY DEFINED LIGHTLY SHADED CIRCULAR AREA ~5 MM IN DIAMETER. THE NEIGHBORHOOD OF THIS SPOT SLOWLY BLENDS INTO THE BACKGROUND. SEEN IN BOTH TRANSMISSION (T) AND REFLECTION (R) MODES. A "NO-GO" DEFECT. |  |
| DRYING PATTERN | AN OBLONG XD (TRANSVERSE) ORIENTED LIGHTLY SHADED REGION ~2-7 CM LONG AND L MM OR GREATER IN WIDTH. REGION IS BOUNDED BY A FAINT LINE. SEEN IN REFLECTION ONLY. A "GO" DEFECT. SPOT DISAPPEARS IN THE MANUFACTURING PROCESS. | 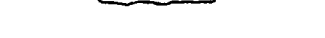 |

| DEFECT | XD1 (TRANSVERSE) | XD2 | MD1 (MACH. DIRECTION) | MD2 | ANOM. DET. STATUS | NO. DISCRETE ANOM. IN MD. | TOTAL (+) ANOMALY AREA | TOTAL (-) ANOMALY AREA | AUTOCAL (SE) (R) | \|SEA PEAK AMP\| (R) | MAX. XD DURATION | MD DURATION | \|SEA PEAK AMP\| (T) | AUTOCAL (SE) (T) | MODE (T OR R) | ACTION (REJECT OR ACCEPT) |
|---|---|---|---|---|---|---|---|---|---|---|---|---|---|---|---|---|
| BASE DIRT | 820 | 822 | 266 | 266 | SEA* | 1 | 2 | 2 | – | – | 3 | 1 | 610 | 563 | T | REJECT |
| BASE DYE | 421 | 427 | 130 | 131 | SEA | 1 | 8 | 2 | – | – | 7 | 2 | 480 | 591 | T | ACCEPT |
| RESIN PICKOFF | 59 | 60 | 140 | 140 | SEA | 1 | 0 | 2 | 613 | 201 | 2 | 1 | 189 | 604 | R | REJECT |
| DRYING PATTERN | 130 | 135 | 163 | 163 | SEA | 1 | 1 | 1 | 605 | 190 | 6 | 1 | 105 | 610 | R | ACCEPT |

\* Sharp Edge Anomaly.

*Fig. 1.*

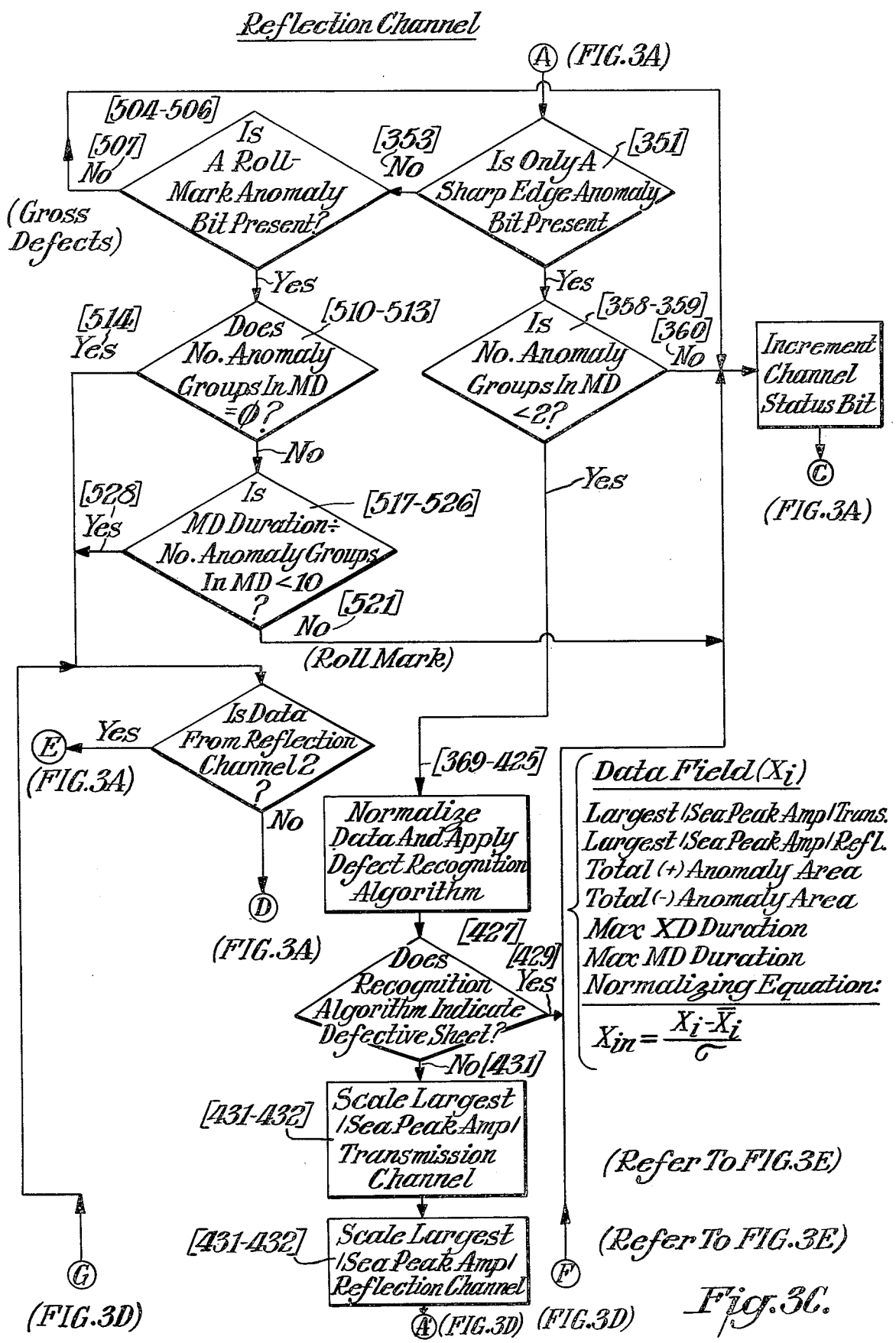

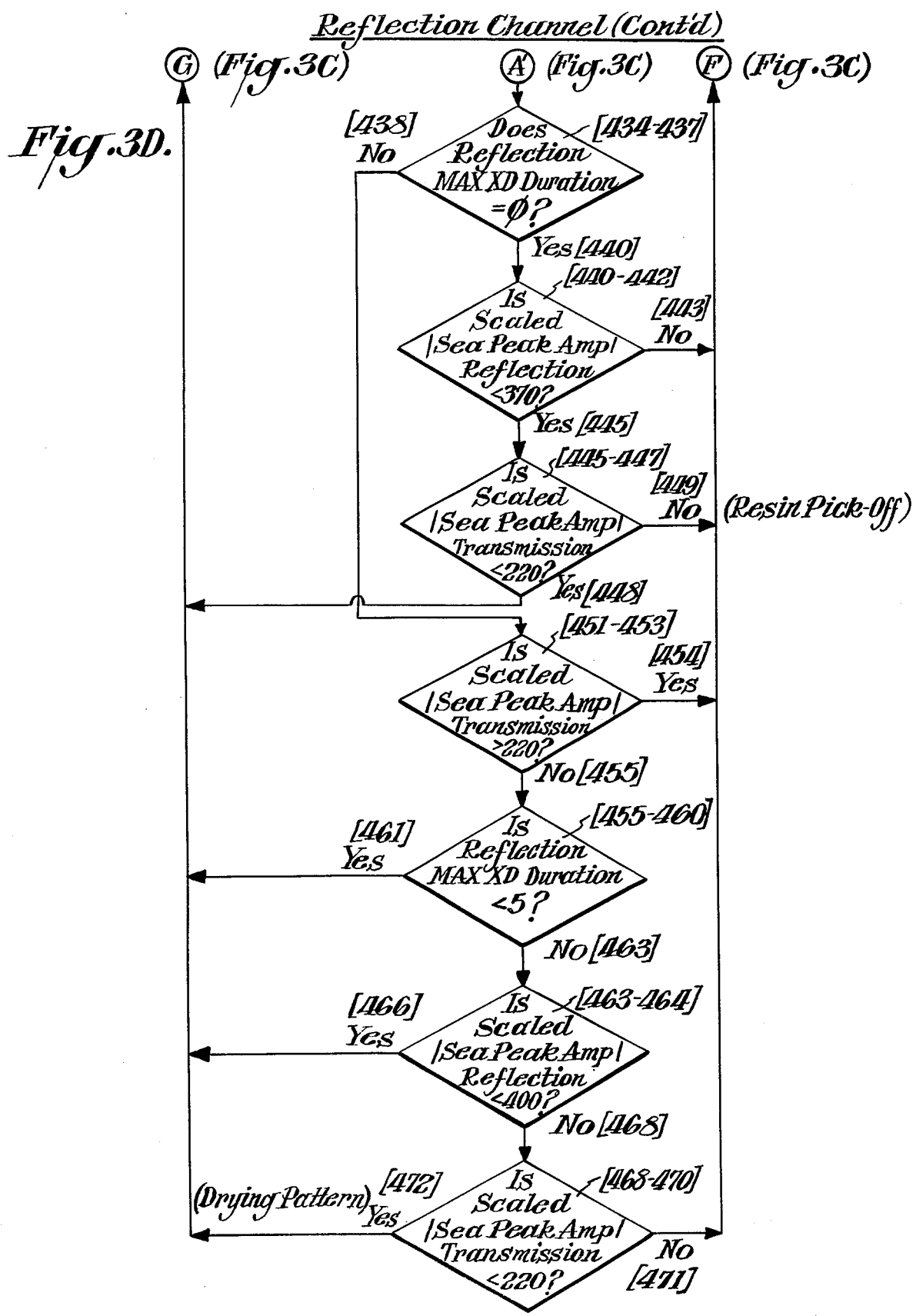

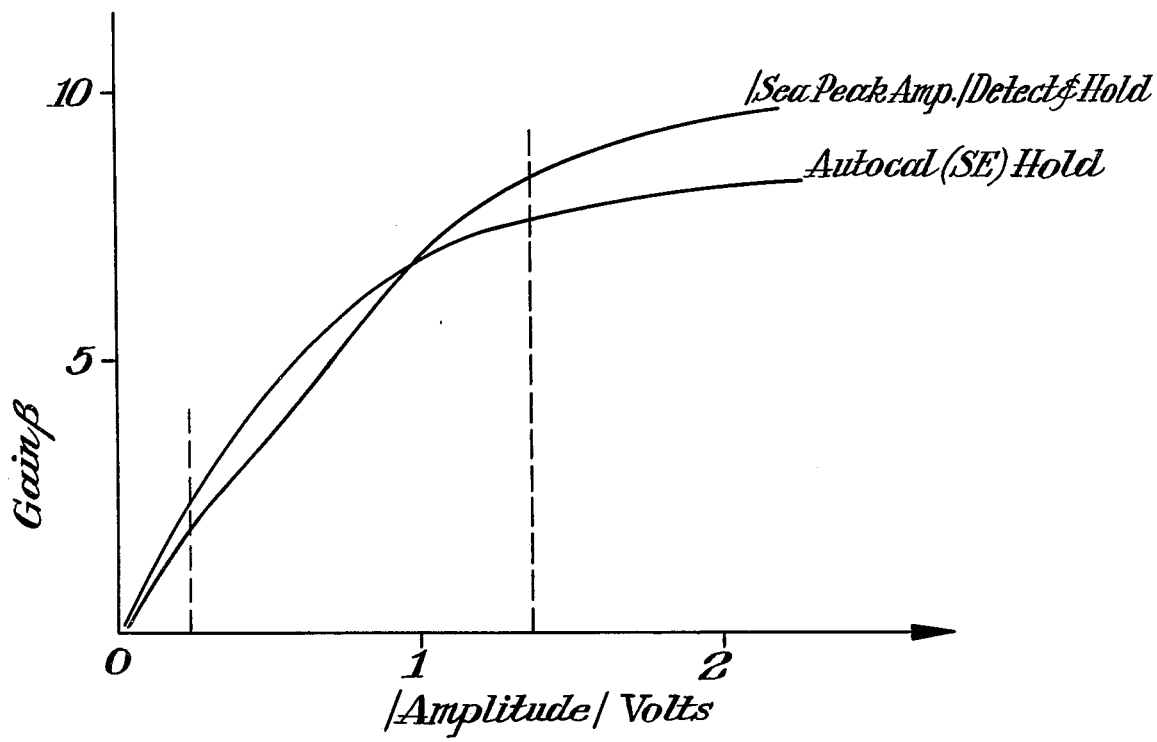

TRANSMISSION CHANNEL SCALING FACTOR $$|\text{SEA PEAK AMP}|\,_{\text{NORM}}^{(\text{TRANS.})} = \frac{|\text{SEA PEAK AMP}|\,(\text{TRANS.})}{\text{AUTOCAL (SE) (TRANS.)}} \times 1000$$

REFLECTION CHANNEL SCALING FACTORS $$|\text{SEA PEAK AMP}|\,_{\text{NORM}}^{(\text{REFL})} = |\text{SEA PEAK AMP}|\,(\text{REFL}) + \frac{|\text{SEA PEAK AMP}|\,(\text{REFL})}{\text{AUTOCAL (SE) (REFL)}} \times 500$$

$$|\text{SEA PEAK AMP}|\,_{\text{NORM}}^{(\text{TRANS})} = |\text{SEA PEAK AMP}|\,(\text{TRANS}) + \frac{|\text{SEA PEAK AMP}|\,(\text{TRANS})}{\text{AUTOCAL (SE) (TRANS)}} \times 500$$

Fig. 3E.

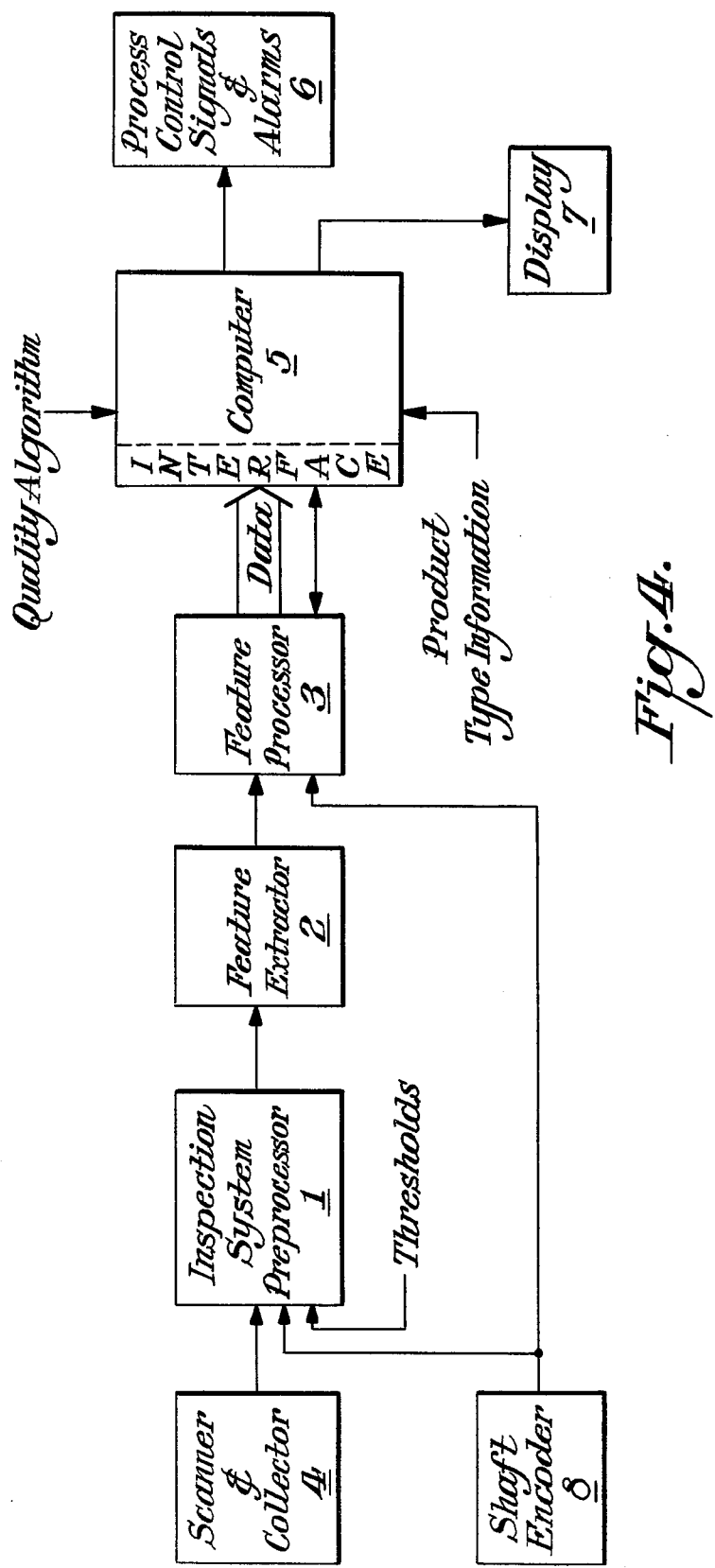

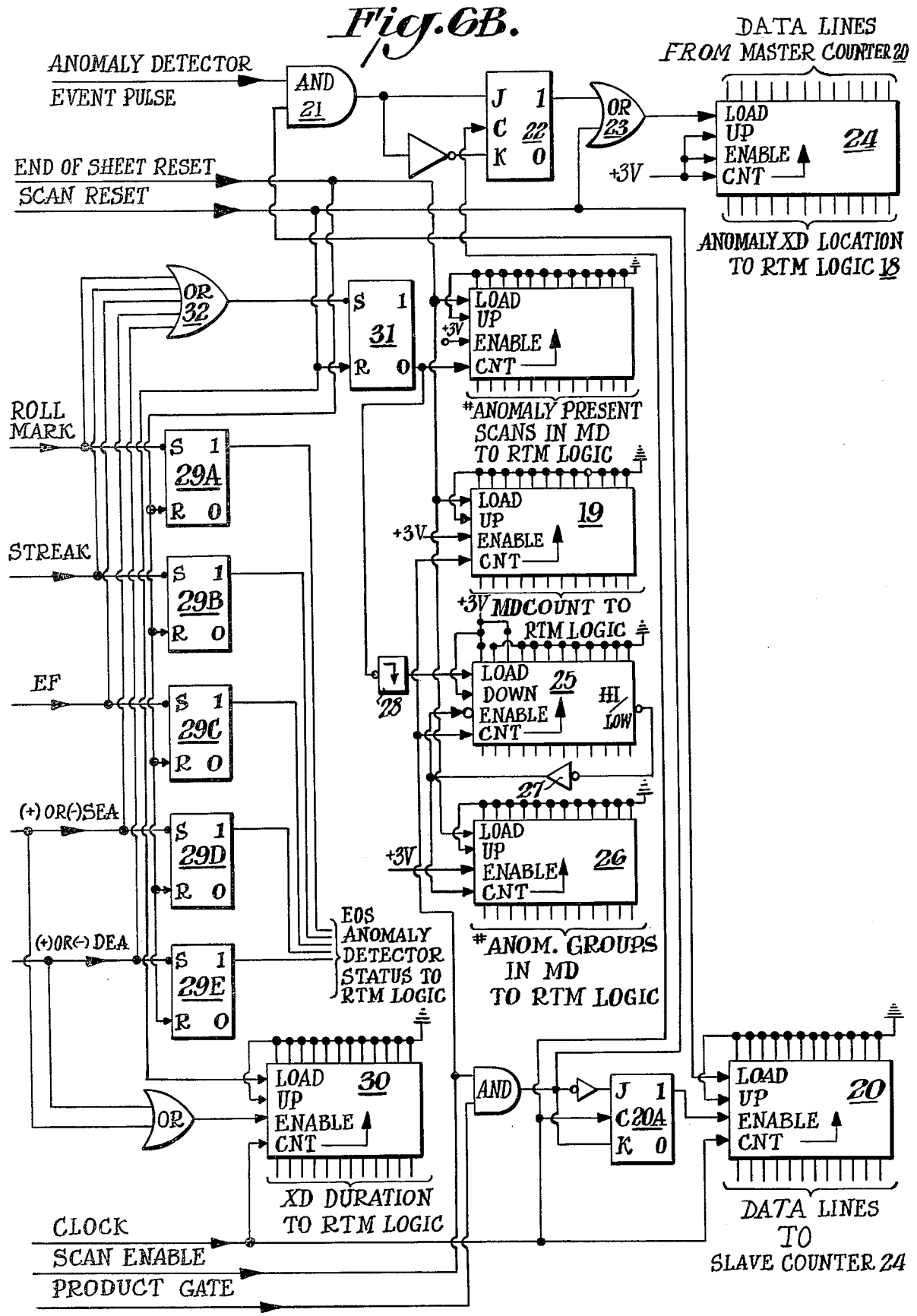

ON-LINE WEB INSPECTION SYSTEM

BACKGROUND OF THE INVENTION

The manufacture of film products such as X-ray photofilm necessitates extremely careful inspection to safeguard against the passage of sheets carrying any defects which can possibly be misinterpreted by radiologists as having a pathological significance after their exposure and development incident to patient diagnosis.

On the other hand, such products as X-ray film inevitably present anomalies in their manufacture which can only be perceived by supersensitive automatic scanning systems, and sometimes by human visual inspectors as well. Some of these anomalies are entirely acceptable, especially in limited number, any under these circumstances do not warrant rejection of the film sheet.

The present invention is an on-line inspection system which is entirely automatic, thereby totally dispensing with human inspectors, so that the inspection process is completely objective. Moreover, the inspection system of this invention is much more sensitive than human visual inspection of the moving web, so that it is capable of detecting anomalies which would otherwise be missed. At the same time, the system can process inspection data so rapidly that film sheet quality can be classified on-the-fly within the time it takes each sheet to clear the inspection station. In addition, the invention correlates feature detection to the limits of each preselected area of a product marketable sheet, thus facilitating the later separation of bad film sheets from good to thereby conserve the maximum area of product possible consistent with rigorous inspection capability.

Finally, the inspection system of this invention is "trainable", in the sense that is can be operated in the course of its inspection task to acquire successive sets of feature signals, thus making it possible to correlate these signals with known visual quality standards at a later time off-line in order to refine inspection acceptance limits, which are thereafter used to meet specified product quality standards.

An important advantage of this invention is that the enhanced inspection sensitivity afforded characterizes the web product to a degree hitherto unknown, thereby permitting greater understanding of the up-stream manufacturing process and the numerous factors which are responsible for the ultimate as-received state of the product web.

CO-PENDING AND RECENTLY ISSUED PATENT ART

This invention is an improvement on the apparatus and method of Application Ser. No. 781,879, now U.S. Pat. No. 4,173,441, property of the common assignee. Preferably, it is used in conjunction with the product zoning invention of Application Ser. No. 853,420 cofiled herewith. In addition, this invention is distinguishable from that taught in German Pat. No. 26 13 921, convention date (Japan) Mar. 31, 1975.

THE DRAWINGS

Figure 6A:
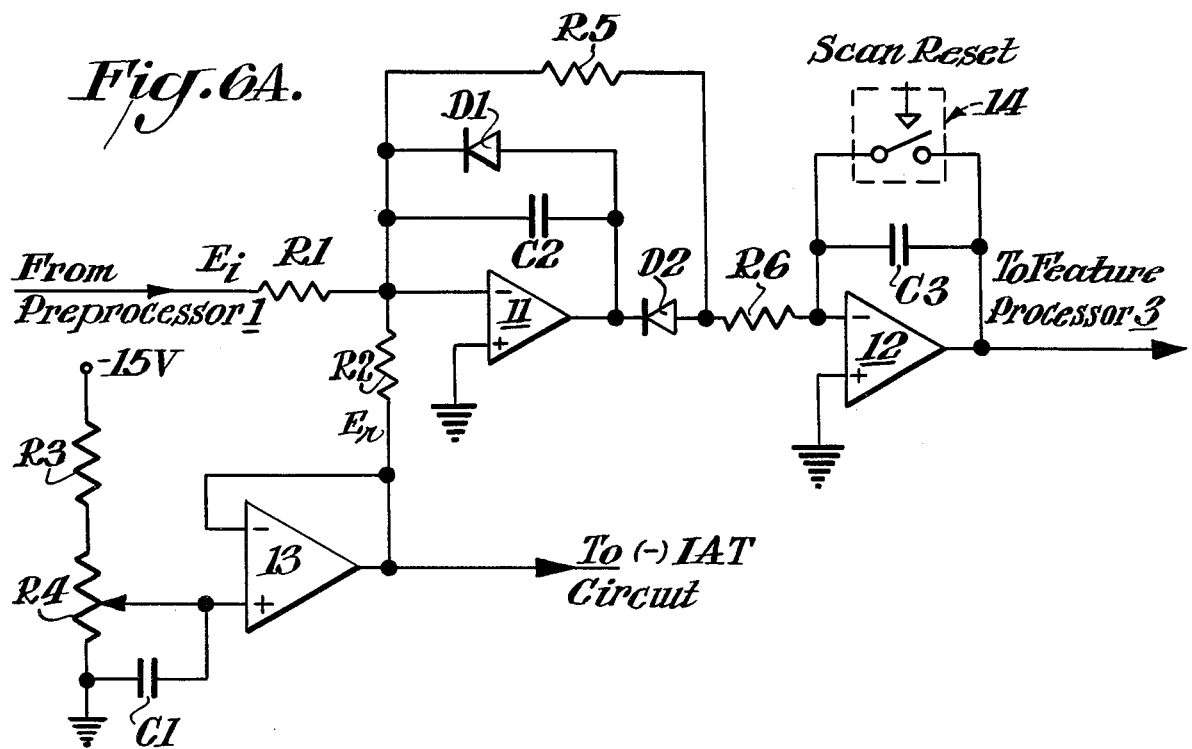
Figure 3A:
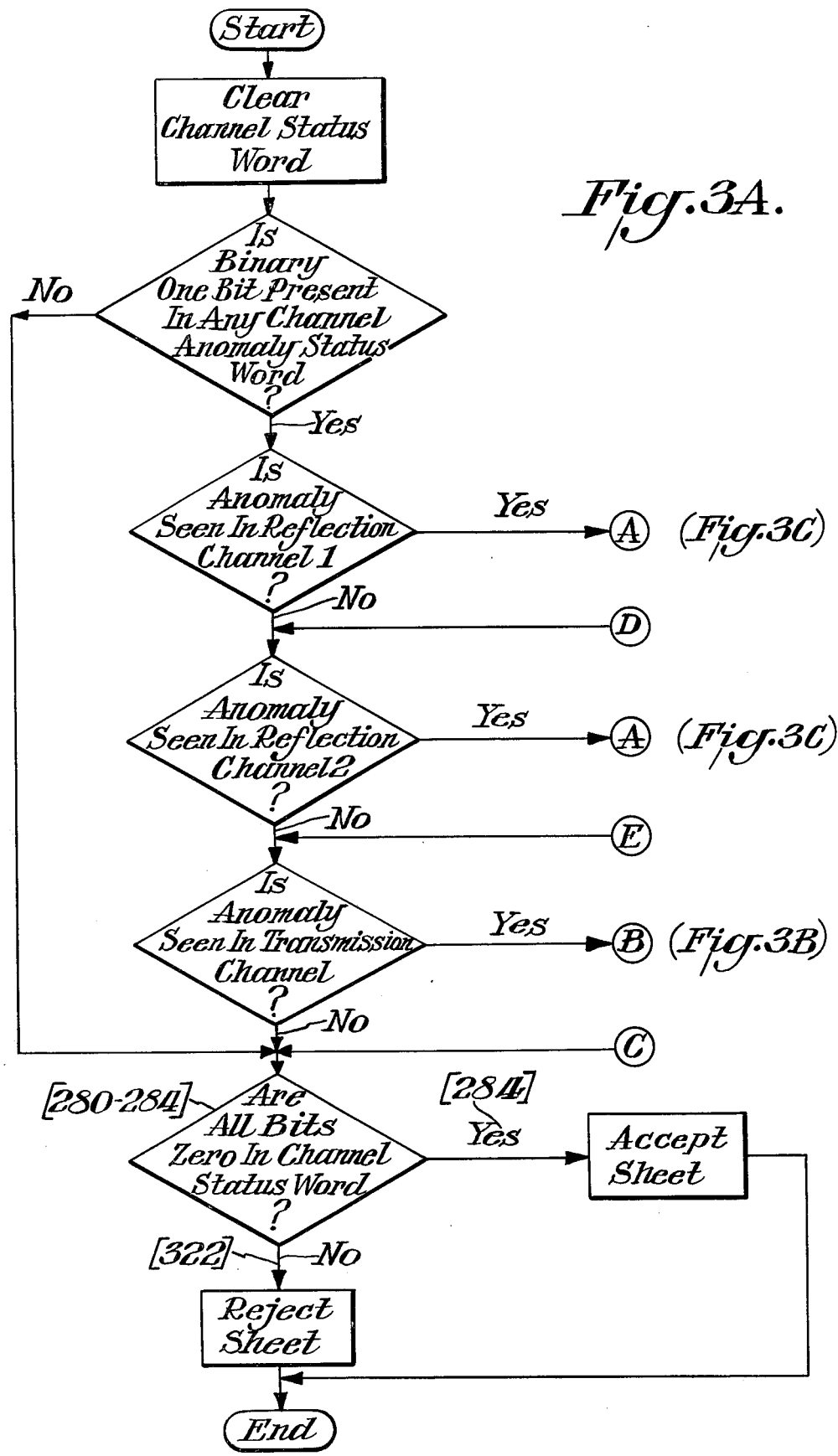
Figure 5B:
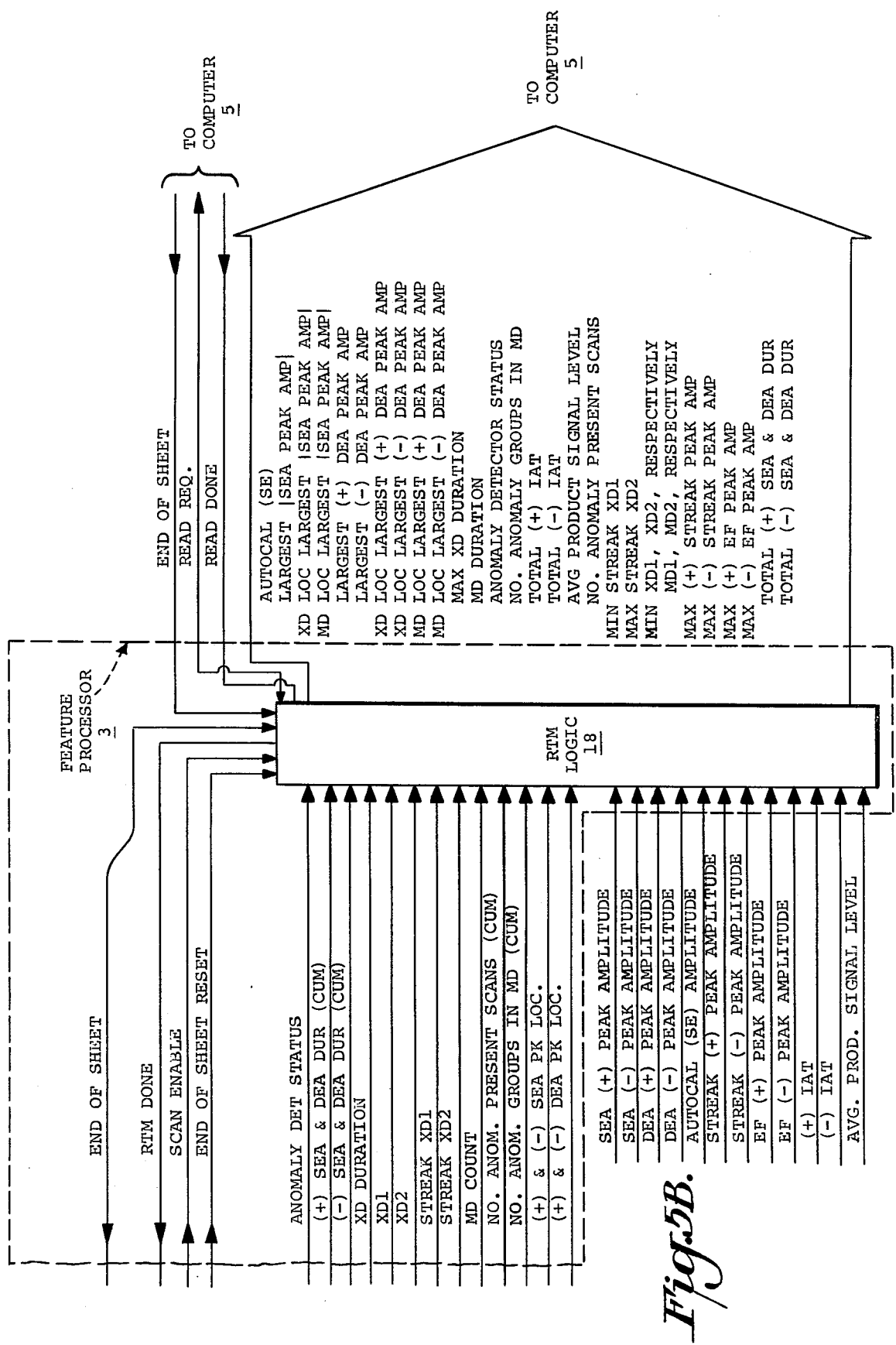
Figure 7A:
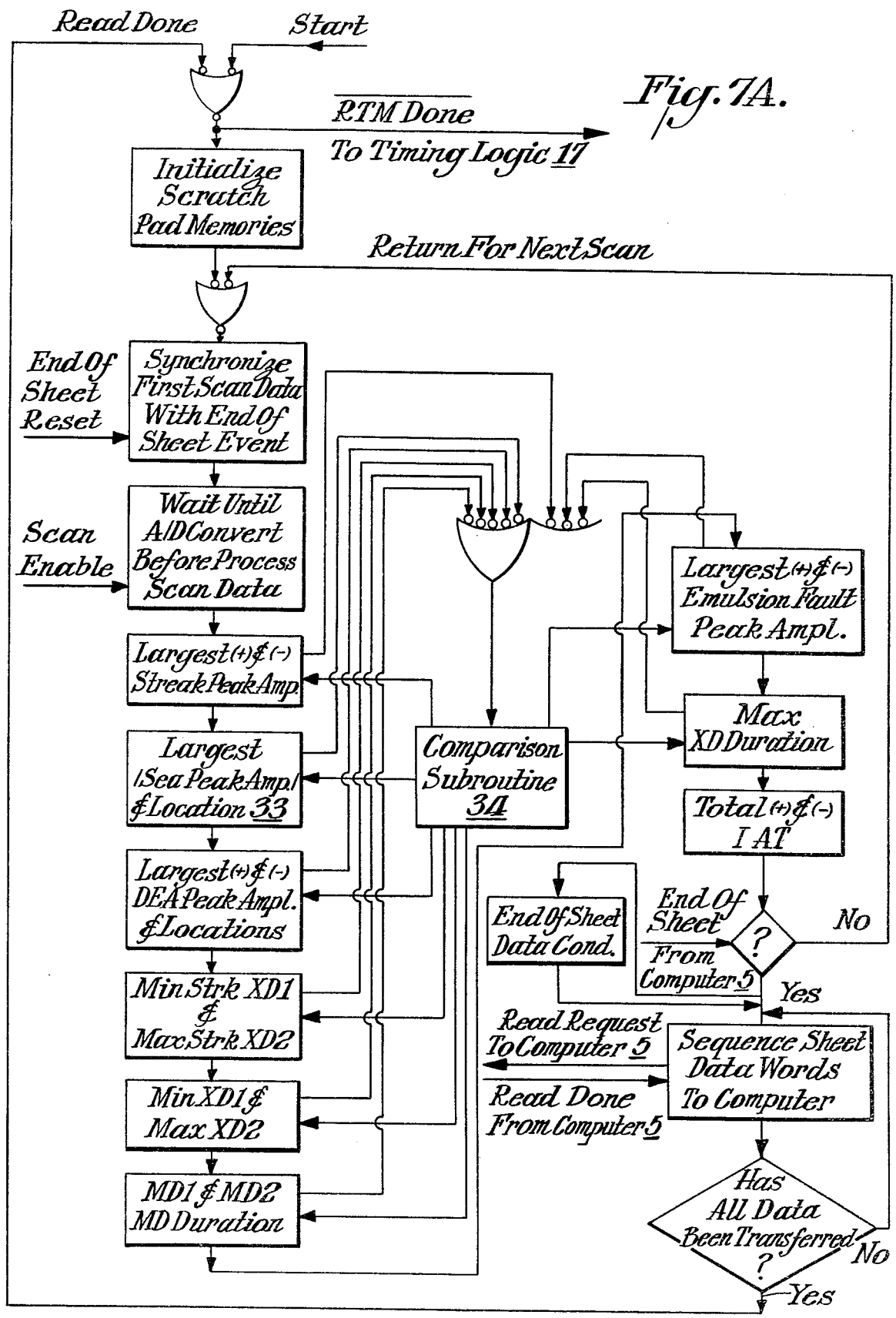
Figure 7B:
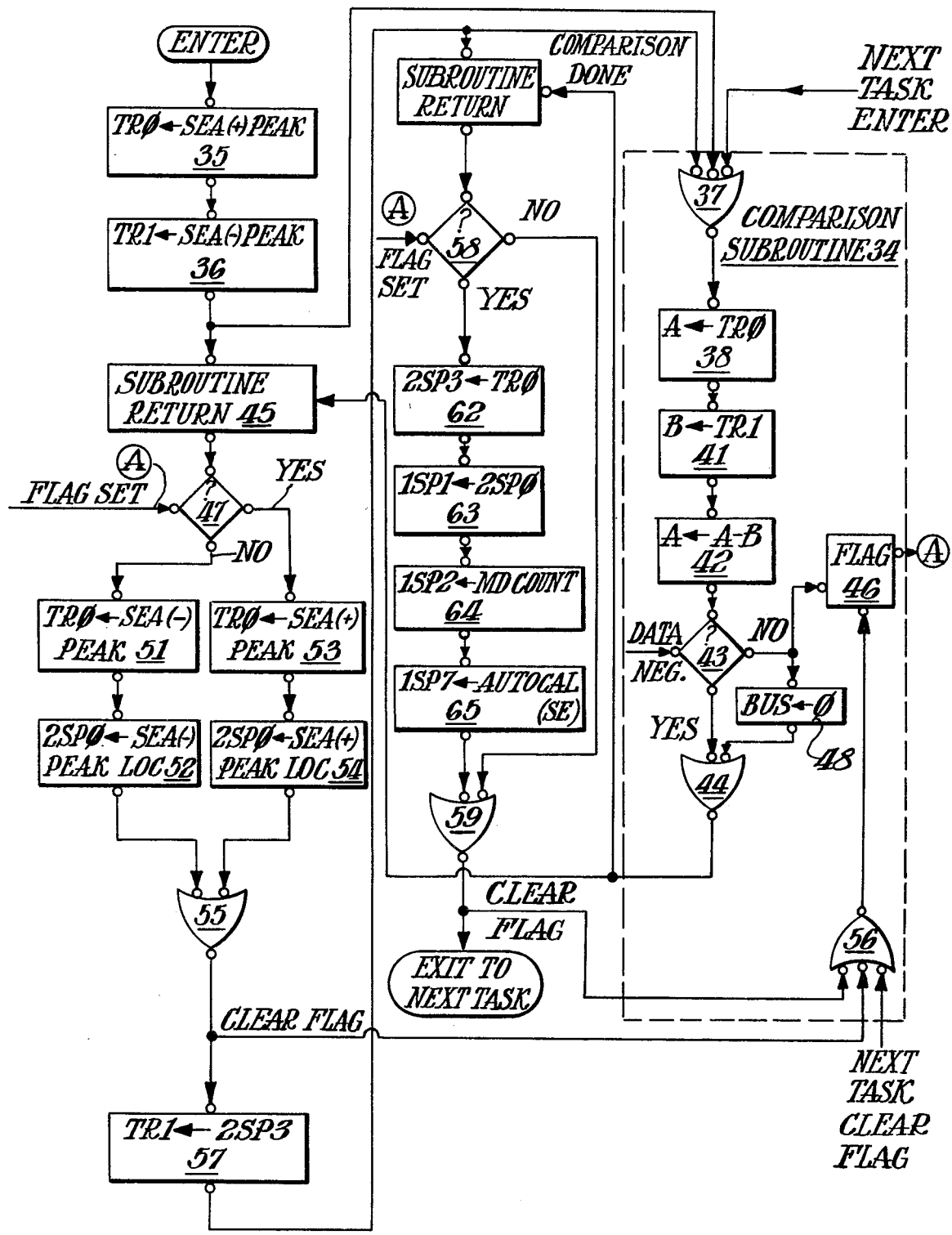

FIG. 1 is a schematic showing of four typical defects found in photographic film manufacture together with their corresponding descriptions and tabulated digital signal characteristics, FIG. 2 is a schematic showing of a sample product sheet showing the MD (Machine Direction) and XD (Transverse Direction) system of coordinates used to define regions containing defects, FIGS. 3A–3D are flow charts detailing the quality algorithms for transmission and reflection inspection channels, respectively, FIG. 3E is a plot showing typical dynamic gain curves for the AUTOCAL (SE) Sharp Edge and SEA (Sharp Edge Anomaly) peak detect and hold circuits, and channel scaling factors, FIG. 4 is a block diagram of the complete inspection system, FIGS. 5A and 5B in lateral extension one with another constitute a flow diagram showing the relationship between the major elements of the signal processing section, namely: the preprocessor, the feature extractor and the feature processor, FIG. 6A is a schematic diagram showing an integrated area above threshold (IAT) circuit, FIG. 6B is a schematic diagram showing feature processor M (MODULE) logic circuitry for generating defect duration, anomaly detector status, peak event location and MD scan statistics, FIG. 7A is a flow chart showing the general arrangement of the RTM (Register Transfer Module) units in the feature processor of FIGS. 5A, 5B and FIG. 7B is a schematic diagram showing a portion of the RTM logic section of FIG. 7A of the feature processor of FIGS. 5A, 5B used for generating several typical end-of-frame feature signals.

A primary object of this invention is to provide apparatus for generating electrical signal characterizing features needed to distinguish defective from non-defective (or marketable) sheet-sized portions of a running product web.

Another object is to provide a method for determining, in real time, at the end of each inspected sheet-sized portion of the running product web, whether the presence, size or areal distribution of detected anomalies is sufficient to reject the sheet.

Another object is to provide a means and method for normalizing (or scaling) the values of the measured scan signal features in order to compensate for differences in the dynamic gains of a multiplicity of feature detector circuits.

DEFINITIONS

FIG. 1 shows four representative X-ray film defects which have been chosen from more than twenty defect types distinguishable by the product quality inspection (PQI) system of this invention. As listed in the table, each defect has its own set of digital signal quantifying attributes detectable over one or more of a sequence of scans across a rapidly moving product web. Of the four defects shown in FIG. 1, only two, i.e., the Base Dirt and the Resin Pickoff are classified as disqualifying, whereas the Base Dye and Drying Pattern anomalies are acceptable (or "GO") types.

Since marketability decisions must be made rapidly (for example, X-ray film manufacture involves slitting and chopping a rapidly running web into 36 cm × 43 cm sheets (14"×17") which can then be further reduced in size later in their manufacture), the system must determine the nature of a scanned defect within the time it takes a sheet-sized portion of the web to pass through the inspection zone. Consequently, the inspection channels (reflection and transmission) must each extract and process approximately 30 features derived from approximately 300 scans across the product every 100 msec.

[This assumes the narrow sheet dimension is oriented in the MD (Machine Direction) and an interscan spacing of 1.5 mm.] Each channel feature processor generates an end-of-frame feature set containing values of all of the characterizing features sensed and accumulated at the end of each inspected sheet for comparison with corresponding defect descriptors stored in minicomputer memory. All features are as listed in FIG. 5B and are defined, in words, as follows:

LARGEST |SEA PEAK AMPLITUDE|—The size of the largest peak of either (+) or (−) polarity produced by the sharp-edge anomaly (SEA) discriminator in any scan in the frame. A detailed description of the sharp-edge anomaly discriminator is disclosed in U.S. Pat. No. 3,843,890. For example, referring to FIG. 2, such a feature might be associated with the small spot (signal maximum) located at XD=500, MD=15.

MIN XD1—The scan direction location of the foremost leading edge of all discrete anomalies [e.g., sharp-edge anomaly (SEA) or diffuse-edge anomaly (DEA)] detected in the frame, corresponding to MIN XD1=500 in FIG. 2.

MAX XD2—The scan direction location of the aftermost trailing edge of all discrete anomalies detected in the frame, corresponding to MAX XD2=1600 in FIG. 2.

MD1—The machine direction location (measured from the top as zero in FIG. 2) of the first scan which detects a discrete anomaly, i.e., MD1=13 in FIG. 2.

MD2—The machine direction location of the last scan to detect a discrete anomaly, i.e., MD2=216 in FIG. 2.

TOTAL (+) SEA & DEA DURATIONS—The sum of the individual scan durations of the digital output pulses generated by the (+) sharp-edge and diffuse-edge anomaly discriminators taken over the entire sheet. For example, referring to FIG. 2, the counts generated as each scan crosses those anomalies producing (+) polarity pulses would be summed together to produce this feature.

TOTAL(−) SEA & DEA DURATIONS—Same as immediately supra, but for the durations of the (−) discriminator output pulses.

XD LOC LARGEST |SEA PEAK AMPLITUDE|—The corresponding cross-product (XD) location of the highest (+) or (−) SEA peak in the sheet, e.g., XD=510 approx., FIG. 2.

MD LOC LARGEST |SEA PEAK AMPLITUDE|—The corresponding machine direction (MD) location of the highest SEA peak in the sheet, e.g., MD=15, FIG. 2.

ANOMALY DETECTOR STATUS—A multi-bit binary word whose bit locations correspond to the detection status of their respective preprocessor anomaly discriminators (roll mark, streak, sharp edge, diffuse edge, and emulsion fault). Those discriminators which detect an anomaly on any given scan in the sheet will cause a binary one to be entered into the respective bit location. One anomaly detector status word is assigned to each inspection channel.

AUTOCAL (SE)—The calibration and scaling signal level produced at the start of each scan by the sharp-edge anomaly (SEA) discriminator as the scanning beam passes over an autocalibration (AUTOCAL) filter. U.S. Pat. No. 3,843,890 discloses how this signal is generated. This value is recorded in the feature processor each time the anomaly detector status word indicates the presence of an anomaly. It is used by the computer to correct the measured end-of-sheet feature values for variations in system optical gains.

LARGEST (+) DEA PEAK AMPLITUDE—The maximum (+) value measured by the diffuse-edge anomaly (DEA) discriminator in any scan in the frame. A detailed description of the diffuse-edge discriminator is set out in U.S. Pat. No. 3,843,890. Such a peak might be associated with the central maximum signal of the large spot located at XD=1500, MD=200, shown in FIG. 2.

XD LOC LARGEST (+) DEA PEAK—The corresponding cross-product (XD) location of the highest (+) DEA peak in the sheet, e.g., XD=1500, shown in FIG. 2.

MD LOC LARGEST (+) DEA PEAK—The corresponding machine direction (MD) location of the highest (+) DEA PEAK in the sheet, e.g., MD=200, shown in FIG. 2.

LARGEST (−) DEA PEAK AMPLITUDE—Same as for LARGEST (+) DEA PEAK AMPLITUDE supra, but for the maximum (−) polarity peak, e.g., the peak located at XD=980, MD=85, in FIG. 2.

XD LOC LARGEST (−) DEA PEAK—Same as XD LOC LARGEST (+) DEA PEAK supra, but for the maximum (−) polarity peak, e.g., XD=980, shown in FIG. 2.

MD LOC LARGEST (−) DEA PEAK—Same as MD LOC LARGEST (+) DEA PEAK supra, but for the maximum (−) polarity peak, e.g., MD=85, shown in FIG. 2.

MAX XD DURATION—The maximum length of time (in XD clock counts) during any scan in the frame of scans that the preprocessed scan signal exceeds the thresholds set into either the sharp-edge anomaly of diffuse-edge anomaly discriminators. For example, since the spot at MD=200 of FIG. 2 is wider in XD than the spot at MD=110, the system would generate a MAX XD DURATION=200 for the sheet.

MD DURATION—The MD distance (in enabled scan counts) between the extreme edges of the first anomaly detected and the last on any given sheet. For example, the anomalous area in FIG. 2 would generate an MD DURATION (MD2−MD1)=216−13=203.

NO. OF ANOMALY GROUPS IN MD—A tally of the number of times that a preprocessor anomaly discriminator detection event is followed by at least N anomaly-free scans. N might typically have a value of five. For example, in FIG. 2, three MD anomaly groups would be counted.

NO. OF ANOMALY PRESENT SCANS—Records the total number of times (in scan counts) that a preprocessor anomaly detector registers the presence of an anomaly on the scanned sheet. In FIG. 2, this value equals 91 scans, i.e., (8+51+32=91), i.e., the difference between limit values plus one.

TOTAL (+) INTEGRATED AREA ABOVE THRESHOLD (IAT)—The value of the sum of the scan integrals, obtained by summing over all scans in the frame the integral of those portions of a zero-based diffuse-edge processed scan signal which exceeds a preset (+) threshold. This feature is used as a measure of sheet blotchiness.

TOTAL (−) INTEGRATED AREA ABOVE THRESHOLD (IAT)—Same as immediately supra, but for (−) polarity scan signals.

AVERAGE PRODUCT SIGNAL LEVEL—The time average during each product scan of the zero-based diffuse-edge processed scan signal level summed over a frame of scans.

MAX (+) EMULSION FAULT PEAK—The maximum (+) value of the emulsion fault signal detected in the sheet. Such a protracted duration signal and the preprocessor circuit for producing it are fully described in U.S. Pat. No. 3,843,890.

MAX (−) EMULSION FAULT PEAK—The same as immediately supra, but for (−) polarity signals.

MAX (+) STREAK PEAK AMPLITUDE—The maximum (+) value of the scanned streak in the sheet measured by the streak detector. A streak detector circuit is fully described in U.S. Pat. No. 4,005,281.

MAX (−) STREAK PEAK AMPLITUDE—Same as immediately supra, but for (−) polarity signals.

MIN STREAK XD1—The foremost leading edge XD position of a MD-oriented streak detected on the sheet.

MAX STREAK XD2—The aftermost trailing edge XD position of a MD-oriented streak detected on the sheet.

CHANNEL STATUS WORD—A three-bit binary word whose bit locations represent the particular channel algorithm which was used to make a defective sheet decision.

THE QUALITY ALGORITHMS

After each inspection channel, feature processor 3 (FIGS. 4, 5A and 5B) accumulates the feature data derived from a frame of scans and, upon command, it transmits the end-of-frame feature set to the computer before the next sheet passes into the inspection zone. Quality algorithms, such as those depicted in the flow charts of FIGS. 3A–3D, cross-referenced by designated step number with the program printout appended, then direct a computer comparison of these end-of-frame features with their corresponding values in a trainable reference feature set to determine the marketability of each sheet.

Although the quality algorithms shown are limited to the particular set of steps and features necessary to distinguish the defects shown in FIG. 1, it is readily apparent to persons skilled in the art that the algorithms can be increased in number to handle additional features required to qualify product according to the presence of other defect classes as well.

At the outset, after the sheet has passed through all of the inspection channels, the algorithm of FIG. 3A clears the contents of the computer channel status word register, then looks for those anomaly detector status words having non-zero values. If an anomaly is present, the algorithm determines which of the three channels sees the anomaly. Either the reflection channel algorithm, FIGS. 3C, 3D or the transmission channel algorithm, FIG. 3B, would then be used at least once before a decision is made to accept or reject the sheet. On the other hand, if none of the anomaly discriminators in any of the three channels detects an anomaly signal, the sheet would be passed as acceptable.

Returning to FIG. 3C, assume that a reflection channel anomaly detector status word has a non-zero value e.g., a binary one bit is in a location indicating the presence of either a sharp-edge or roll mark anomaly. In this case, with the exception of the transmission channel MAX |SEA PEAK AMPLITUDE| feature, only the feature data obtained from the instant channel is used to make a quality decision. The quality algorithm for this channel treats the existence of binary one bits in other locations in the status word to be indicative of a gross defect in the sheet and a reject command would be issued forthwith. Note that, even though a roll mark anomaly may be present on the sheet, its size may not be disqualifying. To resolve this possibility, the ratio of MD duration to the number of discrete anomalies in MD has been found to be a good indicator.

After determining that only one scan or group of scans detects an anomaly, a defect recognition routine may be employed to distinguish which defect class is present on the sheet based on the feature data field $X_i$ shown listed adjacent the action block. A number of defect recognition algorithms can be used. However, it has been found that, in the interest of minimizing decision processing times, either the decision tree classification scheme using piecewise linear discriminant functions to define the interclass hyperplanes, or the nearest-neighbor methods are preferable. Details of the nearest-neighbor routine may be found in correspondence written by P. E. Hart entitled "The Condensed Nearest Neighbor Rule" appearing on pages 515, 516 of the May, 1968 issue of the *IEEE Transactions on Information Theory*. At this point, before the end-of-frame features can be used directly, their values should be normalized to take into account scaling differences. One such scheme is defined by the equation:

$$(X_n)_i = (X_i - \overline{X_i})/\sigma$$

where i=1, ... m (where m is the number of features used) and where $(X_n)_i$ is the normalized end of sheet feature i;

$X_i$ is the uncompensated end of sheet feature i;

$\overline{X_i}$ is the mean of all previously measured training set end of sheet features i;

$\sigma$ is the standard deviation of the previously measured training set end of sheet features i.

Since the recognition algorithm is designed to identify only one class of defect on any given sheet with a given end-of-frame feature set as data input, there is a possibility that a given anomaly may be misclassified due to the existence of two or more defect classes on the same sheet. This pertains particularly to sheets having large dimensions. However, it has been found that this condition rarely occurs in X-ray film manufacture.

For those defects which survive the screening by the recognition algorithm, and after appropriate scaling hereinafter described, the MAX |SEA PEAK AMPLITUDE| feature is used with the MAX. XD DURATION feature to further distinguish the "GO" from the "NO-GO" defect classes such as, for example, the resin pickoff and drying pattern defects having the features tabulated in FIG. 1. Finally, the reflection channel algorithm provides for branching back to two different points in the basic portion of the quality algorithm of FIG. 3A, dependent on whether a "CHANNEL DONE" bit is set in the corresponding location for reflection channel 2 in the channel status word.

FIG. 3E shows diagrammatically the difference in dynamic gain characteristics for the AUTOCAL (SE) and SEA peak detector circuits. This difference has an influence on the measured SEA peak amplitudes as AUTOCAL (SE) voltages vary around a nominal value of 1.0 volt primarily due to optical system gain changes produced by rotating mirror facet-to-facet variations, scanning beam intensity fluctuations, and variations in the AGC for the photo-multiplier detector. By applying the equations shown, the algorithm effectively corrects the measured sharp-edge anomaly (SEA) peak values for a changing AUTOCAL (SE) reference level to bring the two gain characteristic curves into coincidence within the range of maximum sensitivity (e.g., 0.25–1.35 V).

The end result is a more valid peak value measurement for comparison with the stored feature data. As shown in the FIGURE, the forms of the transmission and reflection channel scaling equations differ, since reflection channel data are inherently more sensitive to the hereinbefore mentioned gain fluctuations. Thus, each of the reflection channel scaling equations contains an additional term in order to provide improved sensitivity to these changes.

Figure 3B:
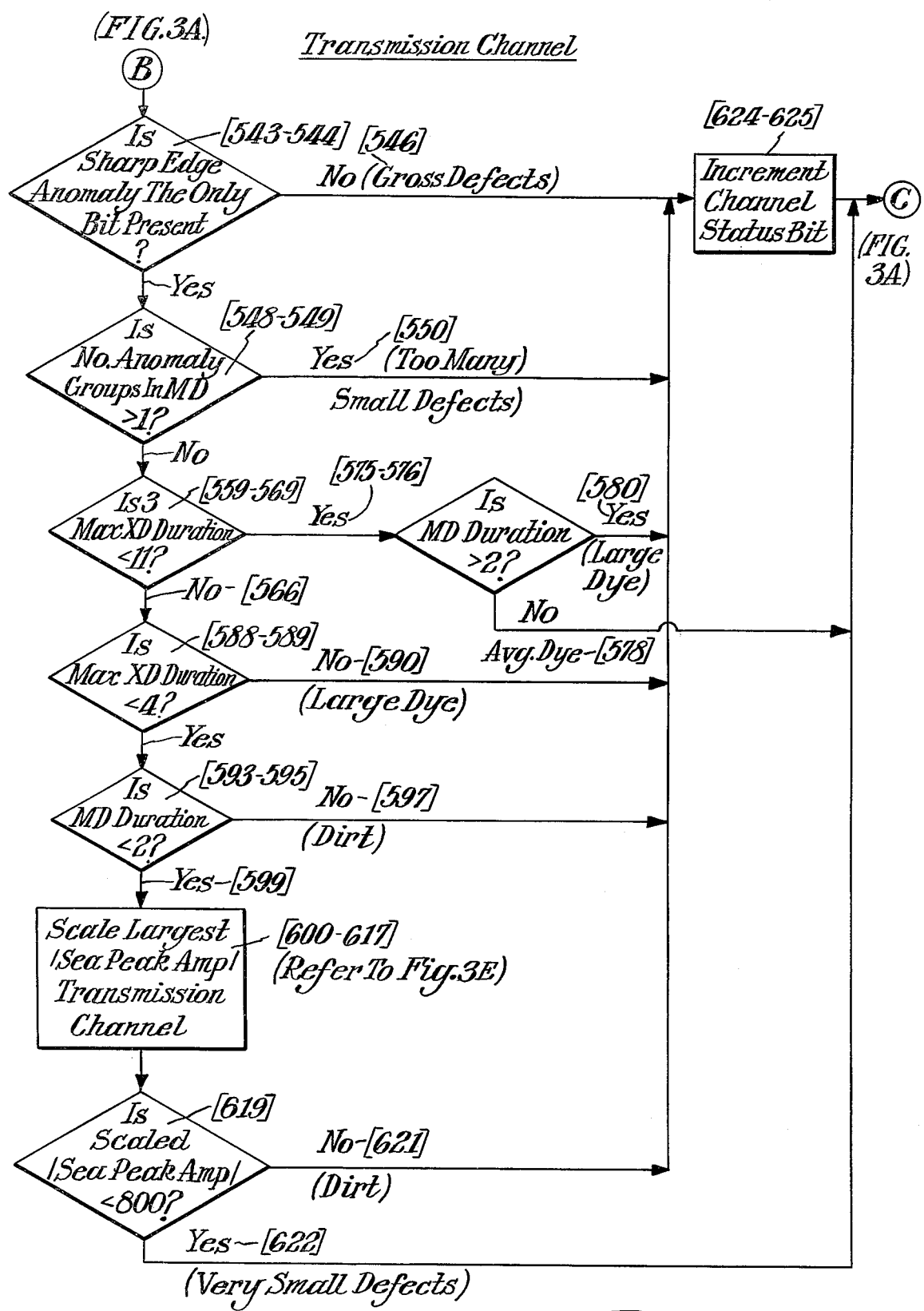
Figure 54:
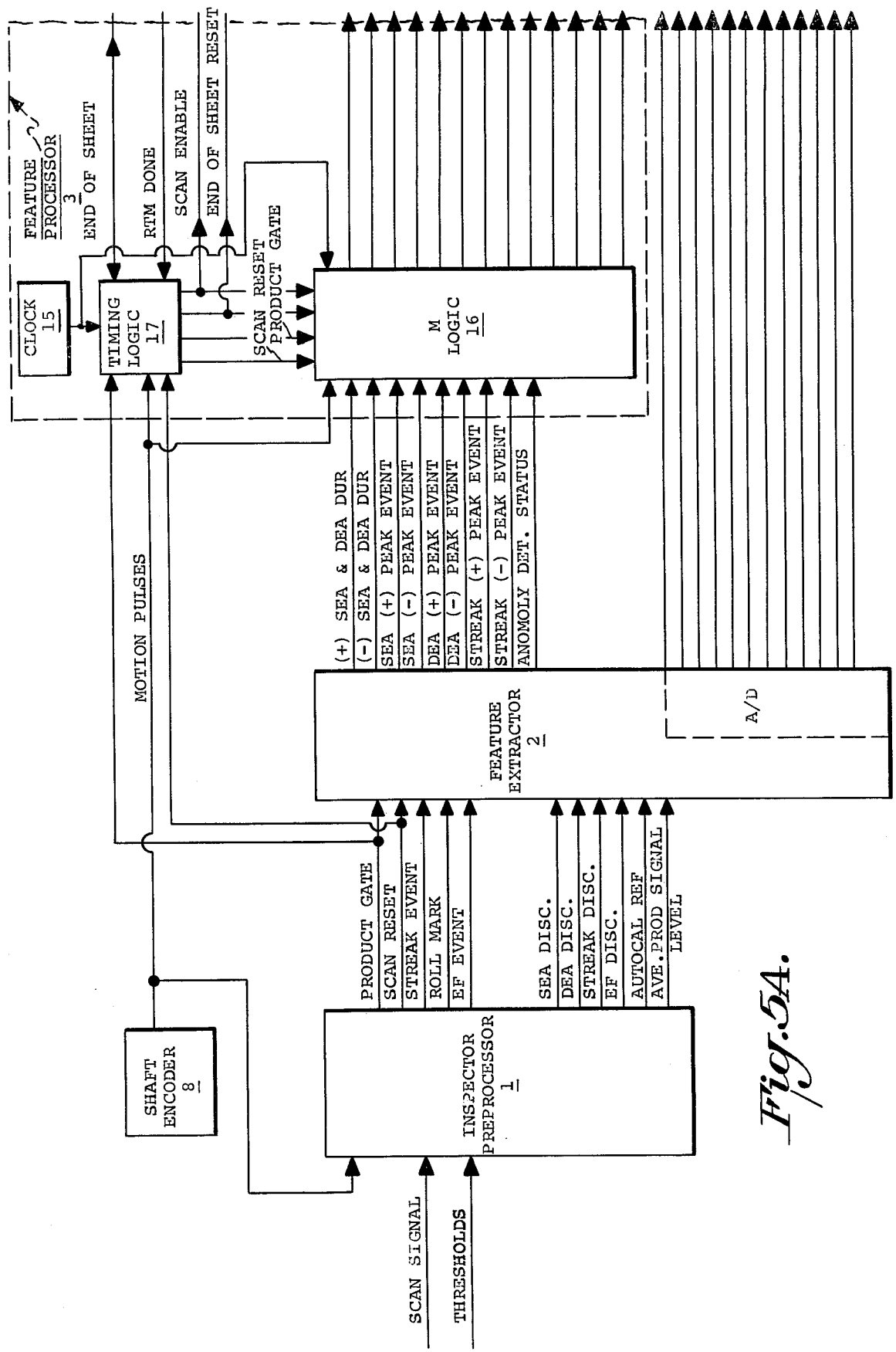

Turning to the transmission channel algorithm of FIG. 3B, note that the steps are generally similar to those of the reflection channel algorithm of FIGS. 3C–3D, in that first the number and then the extent of the anomalous areas are defined before the scaled values of the sheet transmission channel MAX |SEA PEAK AMPLITUDE| are compared with their stored counterparts. The steps shown can be used to distinguish the base dirt defect class from the base dye defect class described by the features tabulated in FIG. 1.

Finally, to ensure that the end-of-frame feature data as received by the computer from the three separate feature processors are consistent, and free from error due to differences in interchannel scan geometries, the computer software includes a provision for compensating the data for differences in scan path length and scan spot velocity using the XD count information from one of the channels as a reference. Scaling the reference XD information using a linear equation of the form $X'=AX+B$ is easily programmed. Interchannel MD offsets are also easily programmed. Consequently, with this scaling, each of the channel end-of-frame feature sets will refer to the identical 0.020"×0.050" (0.5 mm×1.2 mm) areas on each sheet whose boundaries have been defined by clock counts in the XD direction and shaft encoder counts in the MD. [It will be understood that the term "calibrating", as used herein in the Abstract and the claims, is intended to comprehend identifying, normalizing, scaling and the compensating steps hereinbefore mentioned.]

GENERAL SYSTEM DESCRIPTION

FIG. 4 shows in block diagram the product quality inspection (PQI) system, which conforms generally with a recognized pattern recognition model. Associated with this figure is the signal flow diagram of FIGS. 5A and 5B which detail the type of data produced by each of the three major components of the sytem, namely: inspection system preprocessor 1, feature extractor 2, and feature processor 3. The scanner and collector combination 4 typically comprises a rotating multifaceted mirror, a laser illuminator and light-conducting rod of the design described in U.S. Pat. No. 3,843,890. As the laser beam scans the product web, analog pedestal type signals are produced for analysis by the inspection system electronic circuits, hereinafter identified as inspection system preprocessor 1. Each inspection channel preprocessor 1 uses a separate but identical feature extractor 2, and feature processor 3 circuits which are synchronized by a single shaft encoder 8 which rotates at a rate directly proportional to web velocity.

Inspection system preprocessor 1, typically of the type disclosed in U.S. Pat. No. 3,843,890, produces gating signals and contains circuitry to analyze analog pedestal signals for determining the existence of sharp-edge, diffuse-edge and protracted-duration type flaw signals. The emulsion fault (EF) signal is typical of this latter flaw class. Circuits are also known in the art which will detect streaks (U.S. Pat. No. 4,005,281), the abruptness of flaw edges (U.S. Pat. No. 4,011,457), and roll marks (U.S. Pat. No. 3,958,127) according to a set of predetermined threshold levels relative to the product inspected. Finally, such an inspection system preprocessor may generate a calibration signal, such as the AUTOCAL (SE) pulse disclosed in U.S. Pat. No. 3,843,890. The binary and analog signals produced by preprocessor 1 are input to feature extractor 2 which, in turn, derives from each scan certain signal amplitude, duration, peak event and signal area above threshold (IAT) information as functions of the outputs of the various preprocessor discriminator circuits hereinbefore described. (In this connection, "signal area" refers to amplitude x time. Thus, if a line is drawn through an a-c signal representation above its baseline, i.e., the threshold level line $E_r$, the portion lying above this line [or (+) threshold] is denoted the signal area, or, expressed mathematically:

$$\int_{t_0}^{t_1} [E(t) - E_r]dt,$$

where $(t_1-t_0)$ is the scan period,
$E(t)$ is the scan signal, and
$E_r$ is a constant threshold voltage.)

Feature extractor 2, in addition, forms the anomaly detector status word. Finally, the data output from feature extractor 2 is combined with the motion pulses generated by shaft encoder 8 as input to feature processor 3. This latter circuit converts the features developed during individual scans by feature extractor 2 into end-of-sheet features for processing by computer 5. A description of the feature extractor 2 and feature processor 3 circuit components is hereinafter set forth.

At the end of the system is computer 5, typically a DEC PDP-8, which processes the end-of-frame data communicated to it by feature processor 3. The end-of-frame data passes through a commercial interface unit, typically, a DEC M1703 Omnibus Input Interface Unit, when used with a PDP8 minicomputer, which controls the data flow to and from the computer. In accordance with the quality and recognition algorithms previously detailed, computer 5 makes sheet quality decisions and produces output signals for process control and alarms 6 together with a display of defect status 7 in ways known to the art. These decisions are based upon predetermined product quality criteria, i.e., how many anomalies or defects of a certain size per sheet are acceptable, as well as a trainable reference feature set for discrete defect classification hereinafter detailed in the program description. This information is read into the computer main memory before the inspection sequence commences. Although the type of computer used is not critical, computer 5 should have sufficient speed and memory capacity to handle the ninety-odd end-of-sheet features (from three inspection channels) and yet make rapid quality decisions; for example, in the case of X-ray film, data processing time must be within the time required for one sheet to pass through the inspection zone, which is on the order of 100 msec. Furthermore, computer 5 should have sufficient buffering capacity to hold the end-of-sheet data which is generated as each sheet runs the gamut between first and last inspection channels.

A shaft encoder 8, typically a Teledyne-Gurley Model 8625, produces pulses indicative of MD position for use in both inspection system preprocessor 1 and feature processor 3.

FEATURE EXTRACTION

Feature extractor 2 comprises a number of feature selection circuits operating in parallel with one another. One of these is the peak detect and event circuit. Eight of these circuits are used to generate the (+) and (−) peak amplitude (analog) and event pulse (digital) signals with respective inputs from the SEA, DEA, streak, and emulsion fault (EF) discriminators of preprocessor 1. The function of the peak detect and event circuit is to hold for measurement the maximum peak value of the analog signal fed to it in the course of a scan and, simultaneously, to generate an event pulse at the point in time where this maximum occurs. Since both (+) and (−) maxima components of each preprocessor discriminator analog output signal must be determined, two of these peak detect and location circuits are used with each discriminator output. A detailed description of this circuit appears on page 140 of the Nov. 8, 1974 issue of *Electronic Design*.

A second feature selection circuit is the IAT (integration above threshold) circuit shown in FIG. 6A. This circuit computes a value of the integral of the signal area of each PA (Pre-Amplified) scan signal above a given polarity threshold, as a function of time, during each scan. The IAT value of each scan is then tallied by feature processor 3 and is eventually used as a measure of sheet blotchiness. More specifically, this circuit comprises a differential precision rectifier circuit formed around operational amplifier 11, typically a National Semiconductor type LH0062C, in series with a switched integrator circuit formed around a second operational amplifier 12 having similar characteristics. Operational amplifier 13, typically a PHILBRICK 1319, operates as a buffer unity gain amplifier to furnish a constant (−) reference voltage $E_r$ to the summing junction at the inverting terminal of operational amplifier 11, which in turn receives the DEA output voltage signal $E_i$ from preprocessor 1, after voltage to current conversion by resistors R2 and R1, respectively. Resistors R1 and R2 typically each has a 1KΩ value. A ballast resistor R3, typically 10KΩ in series with potentiometer R4, having a range of 0–5KΩ, provides the means to establish a threshold level from the −15V supply. A small capacitor C1, typically of 1 μf value, is used to provide a path to ground for the high frequency components which may be present in the supply voltage. In the feedback loop around operational amplifier 11, resistor R5 has a value of 2KΩ and bypass capacitor C2 a value of 15 pf. Diodes D1 and D2 are typically type IN4454s. Input resistor R6 has a value of 1KΩ and capacitor C3 is typically 0.022 μf. Analog switch 14 is typically a Crystalonics CAG30 and operates to discharge capacitor C3 upon a scan reset signal timed to occur just prior to the product scan. A duplicate IAT circuit, not shown, processes an inverted input signal $E_i'$ using common threshold $E_r$.

A third feature selection circuit (not shown) generates a scan anomaly detector status word to monitor and record, during each scan, those discriminator circuits in preprocessor 1 which detect one or more of the following anomaly types: (1) roll mark, (2) streak, (3) emulsion fault, (4) sharp edge and (5) diffuse edge. This circuit can consist of an array of five flip-flops operating in parallel with one another, each having its set terminal connected to the respective preprocessor discriminator output terminal and its reset terminal connected to the scan reset signal generated by preprocessor 1. Connected to the logic high output terminals of the flip-flop array is a similar parallel flip-flop arrangement, components 29A, 29B, 29C, 29D, and 29E of FIG. 6B, which is used in feature processor 3 to assemble the scan data into an end-of-sheet anomaly detector status word. After the logic states of these flip-flops have been interrogated by the RTM logic section 18 upon an end-of-sheet signal from computer 5, the flip-flops are reset by an end-of-sheet reset signal generated by timing logic 17 (FIG. 5A).

A fourth feature selection circuit, not shown, ORs together the digital pulses produced by the respective (+) and (−) SEA and DEA discriminators to generate corresponding independent (+) and (−) SEA and DEA duration signals. The lengths of the resultant pulse strings indicate the total length of time during each scan that the preprocessed SEA and DEA signals have exceeded the predetermined thresholds that have been set into preprocessor 1 SEA and DEA discriminators. By separately summing the (+) and (−) duration signals over a frame of scans, feature processor 3 produces a total (+) and a total (−) SEA and DEA duration signal which further characterizes the areal extent of the anomalous region of the sheet.

Finally, feature extractor 2 provides the means to convert each scan's AUTOCAL (SE) peak held value into digital form and then transmit it to the RTM Logic section 18 of feature processor 3 for further transmission to computer 5 whenever a SEA or DEA class anomaly is present. As hereinbefore stated, this signal is particularly important for minimizing the effects of scan-to-scan variations due to various non-product related influences.

After the A/D converters of Feature Extractors 2 (FIG. 5A), typically ANALOG DEVICES ADC-10Z-002 types, convert the analog extracted feature signals into digital form as output from feature extractor 2 at the end of each scan, these signals are then transferred by RTM M7317 general purpose interface units, not shown, onto the RTM data bus of feature processor 3 in sequence as ordered by RTM program control.

FEATURE PROCESSOR

The function of each inspection channel feature processor 3 is to compute a list of end-of-sheet digitized anomaly features, generally corresponding to the list of scan features generated by the feature extractor 2, and then read this data into a computer buffer at the end of each sheet's inspection in a form acceptable to rapid computer processing and defect recognition. Both of these steps are completed before the next sheet passes into the inspection zone of a particular inspection channel in order to enable the computer to complete grading and segregating the defective sheets from the product web while feature processor 3 develops the next set of anomaly features.

Referring to FIGS. 5A and 5B, feature processor 3 consists of four major sections: a 5 MHz high frequency digital clock 15, timing logic 17, M logic section 16 for compiling certain scan data, and RTM logic section 18 for composing the scan features into sheet features and transferring the resulting sheet feature set to quality computer 5, which in turn makes the product quality decision.

More specifically, clock 15 generates a binary pulse train which is applied to M logic section 16 for defining XD durations and XD locations of the digital events passed to it by feature extractor 2. In addition, the clock signal is input to timing logic 17 for synchronizing and controlling the operations of the RTM and M logic sections of feature processor 3. The digital logic circuits comprising timing logic 17 are of commercial design for producing the gating and timing pulses hereinafter described.

One of the outputs from timing logic section 17 is the scan enable signal. It is formed by logic means synchronizing the occurrences of a motion pulse from shaft encoder 8 with the product gate signal, originating in preprocessor 1, and a clock pulse from clock 15. The scan enable signal is used in M logic section 16 to increment the MD counter according to product distance travelled so that, regardless of either scan rate or product web velocity variations, the MD separation between the processed scans remains constant. It also can be used in RTM logic section 18 as means to separate features dependent on every scan from those pertaining to the enabled scans only. Finally, after the computer produces an end-of-sheet pulse indicating that it has completed processing the necessary scans of data covering the inspected sheet in accordance with a chop location signal and, provided RTM logic section 18 is ready, timing logic 17 generates an end-of-sheet reset signal to initialize the computational logic in both the RTM and M logic sections in preparation for the next sheet. The chop location signal is generated by a second encoder, not shown, which is mounted on a film chopper at a known distance downstream from the inspection station. It is used by computer 5 to synchronize the feature processor 3 data processing timing with the occurrence of each hypothetical chop line as the web passes through the various scanning locations at the inspection station.

The third major component of feature processor 3 is M logic section 16. This section contains the counting, gating and addressing logic elements which operate to provide both instantaneous and cumulative data on a scan-to-scan basis to RTM logic section 18. FIG. 6B shows a portion of the M logic section circuitry which details the means used to produce the following set of feature signals as output: XD duration, MD count, a tally of the number of anomaly present scans, a tally of the number of anomaly groups in MD, end-of-sheet anomaly detector status and the XD location (in clock 15 counts) of SEA and DEA peaks of either polarity. Although not shown, XD1, XD2, streak XD1 and streak XD2 features are generated by means similar to that used to generate the peak XD location information. More specifically, master counter 20 (FIG. 6B) on each enabled scan produces a series of location pulses on data input lines connected to slave counter 24. Upon receipt of an event pulse at an input terminal of AND gate 21, J K flip-flop 22 is set and immediately reset by a clock pulse. This produces a brief pulse through OR gate 23 to load slave counter 24 with the location data provided to it by master counter 20. The output data lines of slave counter 24 transmit the location data to RTM section 18, for further processing. (In this connection, in order to simplify the showing of FIG. 6B, it is intended that the lower set of data lines on counter 20 connect with the top set of data lines on counter 24; however, these connection lines are not drawn in.) The input data lines of four additional counters (not shown) generating the XD1, XD2, streak XD1 and streak XD2 features are connected to the output data lines of master counter 20. A conventional one-shot, activated upon the occurrence of the leading edge of the first SEA or DEA anomaly detected in the scan, is connected in series with the load terminal of one of the hereinbefore mentioned counters to generate XD1. In a similar fashion a second one-shot triggers on the leading edge of the first streak detected in the scan to load a second counter with STRK XD1. Finally, one-shots operating upon each trailing edge condition are used at the load inputs of the corresponding XD2 and streak XD2 counters to indicate the XD locations of the last trailing edge condition in the scan.

Counters 25 and 26, FIG. 6B, operate cooperatively as a divide by N circuit by means of connecting inverter element 27 for generating a count of the number of anomaly groups scanned in the machine direction which are separated by at least N-enabled scans. In FIG. 6B, the input data lines on counter 25 are arranged to make $N=5$; however, any value of N could just as easily be programmed. This circuitry operates in the following way: Assuming counter 26 has already been reset by an end-of-sheet reset signal and the output of counter 25 is at $\phi$, the first scan to detect any type of anomaly passing through OR gate 32 will set RS flip-flop 31. One-shot 28, connected to the zero terminal of flip-flop 31 strobes counter 25, which loads a value $N=5$, causes the high-low terminal to go low and, by means of inverter 27, enables counter 25 while incrementing counter 26 by one. Should the anomaly still be present on the next scan, the count in both counters 25 and 26 will remain unchanged at $N=5$ and $N=1$, respectively. However, if the next enabled scan is anomaly-free, it will decrement counter 25 to $N=4$. Similarly if the next four enabled scans are "good", counter 25 will be decremented to $N=0$. When counter 25 reaches $N=0$, the high-low terminal changes state and the feedback through inverter 27 disables counter 25. The occurrence of a new anomaly simultaneously loads counter 25 to $N=5$ and increments counter 26 by one.

Finally, although not shown in FIG. 6B, it is easily seen that the same circuitry which is used to generate XD duration data can be extended to generate (+) SEA and DEA duration and (−) SEA and DEA duration signals as well.

The fourth and final major component of feature processor 3 is RTM logic section 18. This section comprises a logic system of register transfer modules (RTM) marketed by Digital Equipment Corporation, which are arranged to collect and process the various feature data and transmit them to computer 5 at the end of each sheet in accordance with the scan-enable and end-of-sheet reset control signals generated by timing logic 17 and the end-of-sheet and read-done pulses from computer 5. A distinguishing feature of the logic system is its ability to calculate and accumulate the feature information needed to determine the identity, location, quantity and extent of the anomalous areas contained within each scanned sheet-sized portion of the product web in real time. The representation of FIG. 7A is a flow chart showing in abbreviated form the arrangement of RTM modules in two concentric feature processing loops. One of these loops, the "inner" one, starts at the "SYNCHRONIZE" block and ends through the "RETURN FOR NEXT SCAN" line, into the OR gate immediately above, whereas the outer loop starts at the "INITIALIZE SCRATCH PAD MEMORIES" and ends through the "READ DONE" line into the OR gate immediately above it. The inner loop comprises the scan tasks which serve to determine the following information for each inspected sheet > the size and XD, MD location of the largest SEA peak
> the size and XD, MD location of the most positive DEA peak
> the size and XD, MD location of the most negative DEA peak
> the smallest streak XD1 value
> the largest streak XD2 value
> the smallest (+) or (−) SEA, or DEA XD1 value
> the largest (+) or (−) SEA, or DEA XD2 value
> the MD1 location of first scan to encounter an anomaly (other than streak)
> the MD2 location of last scan to encounter an anomaly (other than streak)
> the distance between the MD1 and MD2 locations (or MD DURATION)
> the most positive EF peak
> the most negative EF peak
> the most positive streak peak
> the total (+) and (−) IAT
> the most negative streak peak
> the greatest XD duration.

The outer loop, on the other hand, comprises the once per frame task of sequentially interrogating the RTM scratch pad memories storing the inner loop data in addition to registers storing the following data in the M logic section 16 and feature extractor 2:

> average product signal level
> total (+) SEA and DEA duration
> total (−) SEA and DEA duration
> number of anomaly present scans
> number of anomaly groups in MD
> anomaly detector status and transmitting their contents to computer 5.

Preliminary to the interrogating task, data conditioning using data packing techniques may be required for those features which generate large data fields, such as IAT values, to reduce the 16-bit RTM word format to be compatible with the word length requirements of the associated computer 5. In the case of a PDP8 computer, this word length is 12 bits.

A detailed description of the functions and design considerations underlying the use of RTM modules in the loops described is outlined in Bell, Grason and Newell, "Designing Computers and Digital Systems", Digital Press, 1972, and developed by Digital Equipment Corporation. An example of RTM logic circuitry applied to web-inspection apparatus appears in pending patent application U.S. Ser. No. 781,879 supra, filed Mar. 28, 1977.

FIG. 7B is a detailed RTM circuit diagram of blocks 33 and 34 of FIG. 7A showing how the largest |SEA PEAK AMPLITUDE| and location features are calculated from information transmitted on the RTM data bus from XD counter 24 of FIG. 6B of M logic section 16 and digitally converted SEA peak amplitude information from Feature Extractor 2 of FIG. 5A. The characteristics of this circuit are typical of the other RTM circuits used to calculate comparative type features tasked in the scan loop, i.e., the inner loop, of FIG. 7A.

The execution of this task commences when evoke module 35 causes the value of the (+) SEA peak amplitude obtained from feature extractor 2 to be loaded into transfer register zero (TR$\phi$). Similarly, evoke module 36 causes the absolute value of (−) SEA peak amplitude to be loaded into transfer register 1 (TR1). When this step is complete, comparison subroutine circuitry 34 (FIG. 7A) becomes active to determine which of the two peak values is largest. As the program control signal passes OR gate 37, evoke module 38 causes the contents of TR$\phi$ [(+) SEA peak amplitude] to be loaded into register A of arithmetic and logic function, and function selection modules M7301 and M7300, respectively (not shown). Similarly, evoke module 41, causes the contents of TR1 to be loaded into register B. When this step is complete, evoke module 42 causes the difference value A-B formed in the M7300/M7301 module pair to be loaded into its register A. Should this difference be negative, a bus control and terminator module M7332 (not shown) will cause a logic one input to be applied to the condition input of the M7312 two-way branch module 43. A data negative condition indicates that the |SEA (−) peak| is larger than the |SEA (+) peak| and directs program control to exit comparison subroutine circuit 34 directly through a type M1103 OR gate 44 and return to the main program loop by way of subroutine return module 45. On the other hand, if the result is positive, program control will proceed to flag module M7306 46 to set a flag condition on two-way branch 47 and cause evoke module 48 to enter zero onto the RTM data bus before exiting the subroutine through OR gate 44.

Next, dependent on the status of flag 46, two-way branch 47 will cause the larger of ± SEA peak values to be loaded into TR$\phi$ and the corresponding XD peak location into scratch pad memory number 2-word location $\phi$ (2SP$\phi$) by means of evoke modules 51, 52, 53 nd 54, and OR gate 55.

After a clear flag signal is transmitted to clear flag 46 through OR gate 56, evoke module 57 will cause the value of previous largest SEA peak amplitude (stored in 2SP3) to be loaded into TR1 and return to comparison subroutine 34 to determine whether the former largest peak value (loaded into TR1), or the present one (loaded into TR$\phi$), is the larger. Should the former value, now in register B, be the larger, the flag will not be set, as the difference will be negative. In this case, two-way branch 58 will cause the scan data to by-pass the remaining operations in the string and exit through OR gate 59 to the next task, thus preserving the validity of the former value of the largest |SEA PEAK AMPLITUDE| and its location. However, should the present SEA peak value be larger, the flag 46 will be set, which then causes two-way branch 58 to direct the program control to evoke module 62, which causes the current SEA peak data stored in TR$\phi$ to be loaded into 2SP3. In the next step, evoke module 63 causes the corresponding SEA peak XD location data stored in 2SP$\phi$ to be loaded into 1SP1 for temporary storage to await transmission to the computer. Before exiting the task through OR gate 59 evoke modules 64 and 65 will cause the MD count, and the corresponding AUTOCAL (SE) value, to be loaded into 1SP2 and 1SP7, respectively. The AUTOCAL (SE) will be used to normalize the SEA peak amplitude data as described earlier.

Although we have shown a data processing scheme embodying RTM and M logic systems operating in conjunction with a minicomputer in order to reduce processing times to less than 100 m secs, it is practicable to organize a system of one or more microprocessors operating in parallel to provide equivalent data-handling capability.

THE COMPUTER 5 PROGRAM

Turning now to the appended computer program print-out, it will be understood that a collection of appropriately graded product samples must first be assembled by inspection personnel and the measured features of these samples introduced into the computer 5 memory in compatible digital form matching the data acquired during operation of the PQI system. At this point, appropriate algorithms can be devised for accurate classification of film product.

Algorithm derivation with this invention has been achieved by "nearest neighbor" and "decision boundary" techniques, with the outputs being product acceptance or rejection decisions.

For reflection channels, characteristic numbers are utilized according to the "nearest neighbor" approach, such that, if a product sheet is considered "good" at the outset, it is nevertheless automatically considered again, using an algorithm biased to discard marginally good film in order to obtain isolation of all bad film to a very high degree.

There are a number of subroutines associated with this algorithm. Referring to the program print-out, Algorithm 1 commences with line No. 364, at which point inspection data corresponding to a given individual potentially defective product sheet has been acquired and a comparison with product standards is to be made. (Incidentally, the specific product sheet in consideration here would ordinarily have been summarily rejected by inspection techniques in force prior to this invention.)

In interpretation of subsequent program steps, No. 399 is a command to JMP to Subroutine PQNORM (normalize) (line 834 of the program, with the code beginning at line 856).

This brings the magnitude of all characteristic numbers in the feature set to approximately the same level, so that there is no overweighing by any specific number. The reference mean has been established on the basis of absolute data accumulated at a time preceding inspection by the PQI system, a Table of Feature Means being set out starting at line 1363 for (reflection) Channel 1 and starting at line 1386 for (reflection) Channel 3. (In the instant example situation, it was not necessary to employ the "nearest neighbor" technique for (transmission) Channel 2; thus no Mean Table is required for the latter).

Line 841 et seq. is the specific equation used to normalize the raw product data to avoid comparative large number overweighing.

Line 406 denotes another Jump to subroutine command (PQAVEC), commencing at lines 919-920, with the program proper starting at line 944, calling for calculating a distance measure between an acquired particular sheet inspection vector with reference vectors of pre-established product grades. In this connection, a matrix is an example of a vector, so that PQI can use the N-dimensional space defined at line No. 932 to obtain the array of distance measures calculated by this subroutine. Effectively, evaluation consists of determining the point-to-point vector-to-vector distance of a measured characteristic versus a standard characteristic using the equation set out at line 932 and the factors (I,J) are found tabulated in the section between lines 1406 and 1520. The resultant distance measure array, stored in memory, is addressed as VECTBL.

In this program, six distance measures a collected, three for good standards and three for bad.

At line 413, there is a Jump to subroutine command, detailed as PQAMAX, found at line 1066. This effects calculation of the maximum point-to-point vector distance within good limits. The "Pointer to the Vector", line 1079, refers to the specific location in memory where the distance measure array is found. "MODULO", line 1095, refers to the process used for determining which of the good reference vectors corresponds to the maximum.

On program line 419, JMS PQAMIN calls for the procedure for calculating the minimum distance to bad standards; this appears on line 1125.

The foregoing has elicited two numbers, namely, (1) the maximum distance to all good standards and (2) the minimum distance to all bad standards. In the interests of conservatism, the program has been designed to reject all sheets wherein the minimum distance (2) is smaller than the maximum distance (1). In particular, program line 425 prescribes a JMS PQATST (TEST) starting on line 1179 and running through line 1186, which makes a comparison of the above vectors and sets a flag if a reject condition is met on this channel. Then, line 427 checks for the presence of a flag denoting a defective sheet.

This concludes the modified Nearest Neighbor Algorithm.

Lines 431-472 set forth steps further segregating the marginally unacceptable product which had been passed by the "Modified Nearest Neighbor"Algorithm hereinabove detailed. On line 431, "SDPK's" refer to small defect peak amplitude values (i.e., sharp edge anomalies) previously normalized. Line 432 is a Jump to subroutine PQASDN which starts on line 1267 and runs through line 1301. It incorporates SD AUTO (CAL), line 1280, for scaling the normalized transmission and reflection channel |SEA PEAK AMPLITUDE | values in accordance with the equations listed on FIG. 3E; the reflection channel scaling equation is shown on line 1262. NSDPK is the "Scaled Normalized Small Defect Peak Amplitude" value obtained through the reflection channel algorithm, whereas NSDPK2 is the equivalent transmission channel scaled value. This equation corrects for variations in the reflection and transmission channel small defect signal gains as these vary from film type to film type, and even from roll to roll, to obtain measurement consistency.

Lines 434 through 438 list the steps used to identify those anomalies which have practicable zero width, and which could possibly be missed in signal processing. These steps direct action into a branch of the algorithm, handling the zero-width anomaly peak as a special case. In particular, if a zero-width anomaly is detected, action shifts to lines 440-441, where comparison is made between the reflection channel normalized small defect peak amplitude, line 432, and a standard peak amplitude, i.e., per line 440, is the normalized value $\geq 370$? (The 370 limit is basically obtained through trial-and-error.) If the normalized SDPK is less than 370, the sheet is good; otherwise, action goes to line 445, where a check of the transmission channel normalized small defect peak amplitude is made against 220 as the acceptable limit. If greater than 220, the sheet is rejected per line 449 and, if less than 220, the sheet is accepted.

For the non-zero width small defect signal, the algorithm jumps to the AL1A branch at line 451 where a check is made against 220 as the acceptable limit. If the normalized small defect peak amplitude is greater than 220, the sheet is defective. On the other hand, if less than 220, uncertainty still exists. This uncertainty is then resolved should the width be less than 5 as shown on lines 456-460, defining an acceptable sheet. If greater than 5, line 463 appraises the normalized SDPK in a reflection channel and compares it with the limit 400; if the amplitude is less than 400, the sheet is accepted per line 466; if not, line 468 directs a comparison of transmission channel 2 normalized small defect peak amplitude against 200 as a limit. If this amplitude is less than 200, the sheet is accepted; if more, the sheet is rejected per line 471.

The foregoing procedure was evolved as a result of the subtle nature of the resin pick-off defect, which necessitated going beyond the "nearest neighbor" approach to achieve refined inspection results.

Continuing with the reflection channel algorithm at line 353, a JMP AL1F step is used as detailed in lines 504-526 to inquire into the significance of the presence of a roll mark type anomaly as it pertains to sheet quality. Roll marks are generally disqualifying; however, narrow-width sticks marks can be mistaken for roll marks and these latter are passable. Line 504 asks for the anomaly Status Word and in line 505 a data bit comparison is made to determine if just a roll mark bit is set in this status word. In the event more than just the roll mark bit appears in this word, it is indicative that a residual defect class has appeared, and line 507 calls for rejection of the sheet forthwith.

Line 510 obtains the number of anomaly groups in MD seen, from which an average defect MD length is calculated. If the number of anomaly groups in MD seen is zero, the sheet is accepted; if this condition is not present, line 515 saves this number for later use in calculating the average MD length value. Line 517 provides the maximum MD Duration, i.e., the MD distance containing all the defects on the sheet. Then, line 522 calls for dividing MD MAX by NUM(ber)-DEF(ects), thereby giving the average length of the defects. Per line 525, if the quotient is less than 10 clock units (base 10), the sheet is acceptable; if not, the sheet is rejected.

The foregoing completes the Reflection Channel Algorithm, involving the roll mark algorithm which is a separate procedure.

The Transmission Channel Algorithm commences on line 538.

Dye defects are defects in the film base, not in the emulsion per se. These are blue-colored, so that X-ray radiologists do not mistake them for patient indicia. Nevertheless, the degree of severity of this defect may disqualify the sheet.

In contrast, dirt specks could be mistaken by a radiologist as patient indicia, and are also aesthetically undesirable.

Thus, lines 541-546 call for rejection of any sheet except those having a small defect. An additional requirement is that only one defect is tolerable per sheet as per JMS AL(gorithm)NUM(ber)D(efects), lines 548-550, with the subroutine beginning on line 1012.

Line 559 calls for obtaining the XD MAX feature and lines 564-566 compare this feature with a value of 4 clock counts. If XD MAX is greater than or equal to 4 clock pulses it may be indicative of a dye condition. If not, it will be less than 4 clock pulses, and thus possibly be indicative of a dirt defect. In the former event, line 566 directs the algorithm to JMP AL2A for determining the nature of this defect condition with AL2A starting on line 587. In the latter event, should XD MAX be greater than or equal to 4 clock counts, then, by lines 568-570, a comparison is effected to determine whether XD MAX$\leq$10. Should XD MAX be greater than ten, line 571 rejects the sheet. On the other hand, should XD MAX$\leq$10, lines 573-577 determine whether MD MAX$\leq$2. If this condition is true, line 580 rules the sheet acceptable by JMP IAL2 whereas, should MD MAX be greater than two, line 578 calls for sheet rejection.

AL2A begins on line 587. Arrival here occurs because XD MAX was less than 4 clock pulses wide. In lines 587-589 a check of XD MAX is made to determine if it is less than or equal to 3 clock pulses wide. If not, per line 590 the sheet is rejected. If XD MAX is less than 3 clock pulses, the MD width (MD MAX) is compared with 1 clock pulse (lines 592-596). If the MD width is greater than 1 clock pulse, the sheet is rejected per line 597. If not rejected, additional testing is required before a final decision on saleability can be made. To make this decision, a scaling procedure for SEA amplitudes per the first equation, FIG. 3E, is carried out. This procedure corresponds to lines 599-617. Several tests are performed within these eighteen lines of code to check for zero divide by AUTOCAL (line 605) and for a divide overflow (lines 614-615).

If either a zero divide or divide overflow occurs, the sheet is rejected (line 608 and line 616, respectively). If neither a zero divide nor divide overflow occurs, a comparison of the hereinbefore calculated scaled small defect peak amplitude is made with 800 (base 10) per line 619. If the scaled small defect peak amplitude is greater than 800 (base 10), the defect might possibly be a dirt particle, and the sheet is rejected (lines 620-621); if not, the defect most probably is not a dirt particle, and the sheet is accepted per line 622.

This concludes the transmission algorithm.

```
/ PARAMETERS FOR    P Q I    (V2B-B)        PAL8-V10A 08/08/77  PAGE 1

1                       / PARAMETERS FOR    P Q I    (V2B-B)
    2
    3                       /TASK TABLE SETUP - "TASK", "CUR", "INIWT", AND "START"
    4                       / MUST BE DEFINED BY TASK.
    5
    6
    7           1424            *TASK+2+MSGTBL
    8   01424   0000            ZBLOCK  2           /MESSAGE BUFFER IS INITIALLY CLEAR
    9           1604            *TASK+5+TSTABL
   10   01604   0011            CUR%10+CUR          /INITIAL FLAGS #1
   11   01605   4400            START               /INITIAL STARTING ADDRESS
   12   01606   0000            0                   /INITIAL AC IS 0
   13   01607   0001            VERS                /INITIAL MQ IS THE VERSION NUMBER
   14   01610   0000            0                   /INITIAL STEP COUNTER IS 0
   15           2051            *TASK+TFTABL
   16   02051   0000            INIWT               /INITIAL BLOCKING BITS

/ PRODUCT QUALITY ALGORITHM                 PAL8-V10A 08/08/77  PAGE 16

17                       / PRODUCT QUALITY ALGORITHM                      8/8/77
   18
   19           0001            VERS=1
   20                       /
   21                       /
   22                       /%RT    ALGO - PRODUCT QUALITY ALGORITHM
   23                       /
   24                       /%TW    COME HERE FROM "QUAL" WHEN THE SHEET DATA IS
   25                       /       READY FOR QUALITY DECISION PROCESSING. THIS
   26                       /       TASK WILL RUN ONE OF THE QUALITY ALGORITHMS
   27                       /       IF THE DEFECT TYPES PERMIT. IF AN ALGORITHM
   28                       /       FINDS THE SHEET TO BE GOOD, WE SET UP A "GOOD
   29                       /       SHEET" MESSAGE FOR MEMORY AND EXIT VIA "QFIN".
   30                       /
   31                       /
   32
   33
   34           0013            TASK=   ALGO              /PQI QUALITY ALGORITHM
   35           0010            CUR=    ALGOFLD
   36           0000            INIWT=  0                 /INITIALLY RUNNABLE.
   37
   38
   39           0001            FIELD CUR%10
   40
   41           0140            *ALGOPGZ
   42
   43   10140   0000        CH1IST, 0                 /CHANNEL 1 STATUS REGISTER.
   44   10141   0000        CH2IST, 0                 /CHANNEL 2 STATUS REGISTER.
   45   10142   0000        CH3IST, 0                 /CHANNEL 3 STATUS REGISTER.
   46   10143   0000        PQASCR, 0                 /SCRATCH LOCATION.
   47   10144   0000        PQABAD, 0                 /BAD SHEET FLAG.
   48   10145   0000        NSDPK,  0                 /"NORMALIZED" SDPK
   49   10146   0000        NSDPK2, 0                 /"NORMALIZED" SDPK FOR CHANNEL 2
   50
   51
   52           4400            *ALGOLOC
```

```
/ PRODUCT QUALITY ALGORITHM                              PAL8-V10A 08/08/77  PAGE 17

53              /
 54              /
 55              /            DEFINITION OF THE FEATURE ADDRESS LABELS
 56              /
 57              /
 58              /
 59              /FEATURE   RELATIVE              FEATURE
 60              / LABEL    ADDRESS               DESCRIPTION
 61
 62
 63       0000   PSDXD=       00                  /PEAK SMALL DEFECT XD LOCATION
 64       0001   PSDMD=       01                  /PEAK SMALL DEFECT MD LOCATION
 65       0002   PLDXDP=      02                  /PEAK POSITIVE LARGE DEFECT XD LOC.
 66       0003   PLDMDP=      03                  /PEAK POSITIVE LARGE DEFECT MD LOC.
 67       0004   PLDXDN=      04                  /PEAK NEGATIVE LARGE DEFECT XD LOC.
 68       0005   PLDMDN=      05                  /PEAK NEGATIVE LARGE DEFECT MD LOC.
 69       0006   XD1=         06                  /DEFECT STARTING LOCATION - XD
 70       0007   XD2=         07                  /DEFECT ENDING LOCATION - XD
 71
 72       0010   MD1=         10                  /DEFECT STARTING LOCATION - MD
 73       0011   MD2=         11                  /DEFECT ENDING LOCATION - MD
 74       0012   ISTATUS=     12        /*        /INSPECTOR DEFECT STATUS WORD
 75       0013   NUMDEF=      13                  /NUMBER OF DEFECTS IN MD
 76       0014   STK1=        14                  /STREAK STARTING LOCATION - XD
 77       0015   EMULFT=      15                  /EMULSION FAULT REFERENCE
 78       0016   TOTPA=       16        /*        /TOTAL POSITIVE DEFECTIVE AREA (LSB
 79       0017   MSBW1=       17        /*        /MSB'S OF "TOTPA" & "PIAT"
 80
 81       0020   TOTNA=       20        /*        /TOTAL NEGATIVE DEFECTIVE AREA (LSB
 82       0021   MSBW2=       21        /*        /MSB'S OF "TOTNA" & "NIAT"
 83       0022   SDAUTO=      22                  /SMALL DEFECT AUTOCAL
 84       0023   PIAT=        23        /*        /POSITIVE IAT (LSB)
 85       0024   NIAT=        24        /*        /NEGATIVE IAT (LSB)
 86       0025   SDPK=        25                  /SMALL DEFECT PEAK AMPLITUDE
 87       0026   LDPKP=       26                  /POSITIVE LARGE DEFECT PEAK AMPL.
 88       0027   LDPKN=       27                  /NEGATIVE LARGE DEFECT PEAK AMPL.
 89
 90       0030   STK2=        30                  /STREAK ENDING LOCATION - XD
 91       0031   XDMAX=       31                  /MAXIMUM XD DURATION
 92       0032   MDMAX=       32                  /MAXIMUM MD DURATION
 93       0033   STPKP=       33                  /POSITIVE STREAK PEAK AMPLITUDE
 94       0034   STPKN=       34                  /NEGATIVE STREAK PEAK AMPLITUDE
 95       0035   EFPKP=       35                  /POSITIVE EMULSION FAULT PEAK AMPL.
 96       0036   EFPKN=       36                  /NEGATIVE EMULSION FAULT PEAK AMPL.
 97       0037   CHECKW=      37                  /CHECK WORD TERMINATOR (7777)
 98              /
 99              /
100              /
101              /            /*.. SEE DATA FORMAT DETAILS ON THE NEXT PAGE.
102              /
103              /
```

```
/ PRODUCT QUALITY ALGORITHM                    PAL8-V10A 08/08/77  PAGE 18

104              /
105              /
106              /
107              /             DATA FORMAT DETAILS FOR PACKED DATA WORDS
108              /
109              /
110              /   FEATURE              DATA DESCRIPTION
111              /   LABEL
112              /
113              /
114              /   ISTATUS      BIT 0-4  NOT USED (ZERO)
115              /                     5   ROLL MARK
116              /                     6   STREAK
117              /                     7   SMALL DEFECT
118              /                     8   LARGE DEFECT
119              /                     9   EMULSION FAULT
120              /                    10   SPLICE
121              /                    11   EDGE DEFECT
122              /
123              /
124              /   TOTPA        THE 12 LSB'S OF THE TOTAL POSITIVE
125              /                DEFECTIVE AREA.
126              /
127              /
128              /   MSBW1        BIT 0-4   NOT USED (ZERO)
129              /                    5-8   MSB'S OF THE "PIAT"
130              /                   9-11   MSB'S OF THE "TOTPA"
131              /
132              /
133              /   TOTNA        THE 12 LSB'S OF THE TOTAL NEGATIVE
134              /                DEFECTIVE AREA.
135              /
136              /
137              /   MSBW2        BIT 0-4   NOT USED (ZERO)
138              /                    5-8   MSB'S OF THE "NIAT"
139              /                   9-11   MSB'S OF THE "TOTNA"
140              /
141              /
142              /   PIAT         THE 12 LSB'S OF THE POSITIVE INTEGRATE
143              /                ABOVE A THRESHOLD VALUE.
144              /
145              /
146              /   NIAT         THE 12 LSB'S OF THE NEGATIVE INTEGRATE
147              /                ABOVE A THRESHOLD VALUE.
148              /
149              /

/ PRODUCT QUALITY ALGORITHM                    PAL8-V10A 08/08/77  PAGE 19

150              /
151  14400  7300  START,  CLB
152  14401  4020          CAL
153  14402  0004          SUSPND         /GO TO SLEEP FOR NOW.
154              /
155              /
156              /       FIRST DETERMINE WHAT DEFECTS WERE SEEN ON THIS SHEE
157              /
158              /
```

| | | | | | |
|---|---|---|---|---|---|
| 159 | 14403 | 7300 | | CLB | |
| 160 | 14404 | 7431 | | SWAB | /INSURE EAE MODE "B" !! |
| 161 | | | | | |
| 162 | 14405 | 1067 | | TAD CH1BAS | /GET THE CH 1 STATUS REGISTER. |
| 163 | 14406 | 4777' | | JMS GETDAT | |
| 164 | 14407 | 0012 | | ISTATUS | |
| 165 | 14410 | 3140 | | DCA CH1IST | /SAVE IT FOR LATER. |
| 166 | 14411 | 1140 | | TAD CH1IST | |
| 167 | 14412 | 7640 | | SZA CLA | |
| 168 | 14413 | 7301 | | CLB IAC | /PUT 1 IN "PQASCR" IF A DEFECT IS |
| 169 | 14414 | 3143 | | DCA PQASCR | / PRESENT |
| 170 | | | | | |
| 171 | 14415 | 1070 | | TAD CH2BAS | /NOW DO CH 2. |
| 172 | 14416 | 4777' | | JMS GETDAT | |
| 173 | 14417 | 0012 | | ISTATUS | |
| 174 | 14420 | 3141 | | DCA CH2IST | /SAVE FOR LATER |
| 175 | 14421 | 1141 | | TAD CH2IST | |
| 176 | 14422 | 7640 | | SZA CLA | |
| 177 | 14423 | 7305 | | CLB IAC RAL | /ADD A 2 INTO "PQASCR" IF DEFECT IS |
| 178 | 14424 | 1143 | | TAD PQASCR | / PRESENT |
| 179 | 14425 | 3143 | | DCA PQASCR | |
| 180 | | | | | |
| 181 | 14426 | 1071 | | TAD CH3BAS | /AND LASTLY CH3. |
| 182 | 14427 | 4777' | | JMS GETDAT | |
| 183 | 14430 | 0012 | | ISTATUS | |
| 184 | 14431 | 3142 | | DCA CH3IST | /SAVE FOR LATER |
| 185 | 14432 | 1142 | | TAD CH3IST | |
| 186 | 14433 | 7640 | | SZA CLA | |
| 187 | 14434 | 7307 | | CLB IAC RTL | /ADD A 4 INTO "PQASCR" IF DEFECT IS |
| 188 | 14435 | 1143 | | TAD PQASCR | / PRESENT. |
| 189 | 14436 | 3143 | | DCA PQASCR | |
| 190 | | | | | |
| 191 | 14437 | 1140 | | TAD CH1IST | /NOW FORM THE COMBINED STATUS WORD. |
| 192 | 14440 | 7421 | | MQL | |
| 193 | 14441 | 1141 | | TAD CH2IST | |
| 194 | 14442 | 7501 | | MQA | |
| 195 | 14443 | 7421 | | MQL | |
| 196 | 14444 | 1142 | | TAD CH3IST | |
| 197 | 14445 | 7501 | | MQA | |
| 198 | 14446 | 3057 | | DCA SHSTAT | /SAVE IT WHERE OTHERS CAN USE IT. |

/ PRODUCT QUALITY ALGORITHM          PAL8-V10A 08/08/77   PAGE 20

| | | | | | |
|---|---|---|---|---|---|
| 199 | | | / | | |
| 200 | | | / | | |
| 201 | | | / | NOW DETERMINE WHAT WE ARE TO DO | |
| 202 | | | / | | |
| 203 | | | / | | |
| 204 | 14447 | 1055 | | TAD PQRSCD | |
| 205 | 14450 | 1376 | | TAD (-4) | |
| 206 | 14451 | 7710 | | SPA CLA | |
| 207 | 14452 | 5332 | | JMP ALG10 | /NO |
| 208 | | | / | | |
| 209 | | | / | | |
| 210 | | | / | CALL ON THE PROPER ALGORITHM | |
| 211 | | | / | | |
| 212 | | | / | | |

```
213  14453  3144           DCA POABAD      /CLEAR THE BAD SHEET FLAG, SOMEONE
214                                        / WILL SET IT FOR A BAD SHEET !
215
216  14454  1143           TAD POASCR      /FORM A JUMP INSTRUCTION FROM THE
217  14455  1375           TAD (JMP I ALGOTL)  /CHANNEL DEFECT INFORMATION,
218  14456  3257           DCA .+1
219  14457  7402           HLT             /AND EXECUTE IT.
```

/ PRODUCT QUALITY ALGORITHM                    PAL8-V10A 28/08/77   PAGE 21

```
220                /
221                /
222                /
223                /         DISPATCH TABLE OF ALGORITHMS
224                /
225                /         FOR DIFFERENT CHANNEL COMBINATIONS
226                /
227                /
228  14460  4552   ALGOTL,  ALG11           /0, NO DEFECTS.
229  14461  4470            CHL1            /1, CHANNEL 1
230  14462  4472            CHL2            /2, CHANNEL 2
231  14463  4503            CHL12           /3, CHANNELS 1 & 2
232  14464  4506            CHL3            /4, CHANNEL 3
233  14465  4510            CHL13           /5, CHANNELS 1 & 3
234  14466  4513            CHL23           /6, CHANNELS 2 & 3
235  14467  4516            CHL123          /7, CHANNELS 1, 2 & 3
236                /
237                /
238                /        ALGORITHM SEQUENCES FOR THE CHANNEL COMBINATIONS
239                /
240                /
241  14470  4774'  CHL1,    JMS AL1
242  14471  5322            JMP ALG1
243
244  14472  4773'  CHL2,    JMS AL2
245  14473  1144            TAD POABAD      /DID ANYONE SAY BAD SHEET ?
246  14474  7650            SNA CLA
247  14475  5301            JMP .+4
248  14476  1372            TAD (1004)
249  14477  3072            DCA LASTQL
250  14500  5332            JMP ALG10
251
252  14501  1371            TAD (1005)      /SET THE QUALITY MESSAGE FOR "CH2
253  14502  5352            JMP ALG11       /ONLY GOOD SHEET" AND EXIT.
254
255  14503  4774'  CHL12,   JMS AL1
256  14504  4773'           JMS AL2
257  14505  5322            JMP ALG1
258
259  14506  4770'  CHL3,    JMS AL3
260  14507  5322            JMP ALG1
261
262  14510  4774'  CHL13,   JMS AL1
263  14511  4770'           JMS AL3
264  14512  5322            JMP ALG1
265
266  14513  4773'  CHL23,   JMS AL2
267  14514  4770'           JMS AL3
268  14515  5322            JMP ALG1
269
```

```
270    14516  4774' CHL123,  JMS AL1
271    14517  4773'          JMS AL2
272    14520  4770'          JMS AL3
273    14521  5322           JMP ALG1
```

/ PRODUCT QUALITY ALGORITHM                     PAL8-V10A 08/08/77  PAGE 22

```
274                    /
275                    /
276                    /
277                    /    RETURN HERE TO DETERMINE THE SHEET QUALITY
278                    /
279                    /
280    14522  7300  ALG1,  CLB
281    14523  1144         TAD PQABAD       /DID ANYONE SAY BAD SHEET ?
282    14524  7640         SZA CLA
283    14525  5330         JMP .+3          /YES, GO ON.
284    14526  1367         TAD (1001)       /NO, SAY  G O O D  SHEET !!!
285    14527  5352         JMP ALG11        /ALL DONE, GO TO TASK EXIT.
286
287    14530  1366         TAD (1002)
288    14531  3072         DCA LASTQL
289                    /
290                    /
291                    /
292                    /
293                    /
294    14532  1057  ALG10, TAD SHSTAT       /ANY DEFECTS ON THIS SHEET ?
295    14533  7650         SNA CLA
296    14534  5352         JMP ALG11        /NO, JUST EXIT, SAYING NO INFO.
297    14535  7410         SKP
298    14536  7000         NOP              /RESERVED LOCATION
299                    /
300                    /
301                    /
302                    /
303                    /
304    14537  7300         CLB
305    14540  1055         TAD PQRSCD
306    14541  7450         SNA
307    14542  5353         JMP ALG12
308
309    14543  1376         TAD (-4)
310    14544  7650         SNA CLA
311    14545  5353         JMP ALG12
312
313    14546  1365         TAD (PQRS)
314    14547  4020         CAL
315    14550  0003         PUN
316    14551  5200         JMP START
317
318
319    14552  3072  ALG11, DCA LASTQL       /SAVE THE VALUE FOR THE QUALITY
320                                         / MESSAGE FOR THIS SHEET.
321
322    14553  7300  ALG12, CLB
323    14554  1364         TAD (QFIN)       /NOW RUN THE "FINISH SHEET" TASK.
324    14555  4020         CAL
325    14556  0003         RUN
326    14557  5200         JMP START        /ALL DONE, SLEEPY TIME AGAIN.
```

/ PRODUCT QUALITY ALGORITHM                PAL8-V10A 08/08/77  PAGE 23

```
327
328                    /
329    14564  0015
330    14565  0014
331    14566  1002
332    14567  1001
333    14570  5400
334    14571  1005
335    14572  1004
336    14573  5200
337    14574  4600
338    14575  5560
339    14576  7774
340    14577  6321
341           4600         PAGE
```

/ PRODUCT QUALITY ALGORITHM                PAL8-V10A 08/06/77  PAGE 24

```
342                /
343                /
344                /
345                /      ALGORITHM FOR CHANNEL 1 DEFECTS ONLY
346                /
347                /
348    14600  0000   AL1,  0
349    14601  7300         CLB
350    14602  1140         TAD CH1IST      /GET THE CHANNEL 1 STATUS REGISTER.
351    14603  0377         AND (7757)      /ONLY SMALL DEFECT ?
352    14604  7640         SZA CLA
353    14605  5776'        JMP AL1F        /NO, TRY FOR ROLL MARK.
354                /
355                /
356                /
357
358    14606  4775'        JMS ALNUMD      /GO CHECK FOR ONLY 1 DEFECT/SHEET.
359    14607  0001         1
360    14610  5774'        JMP AL1G        /MORE THAN 1 DEFECT PRESENT, GO SAY
361                                        /REJECT THIS SHEET.
362                /
363                /
364                /      WE HAVE A SHEET FOR THE ALGORITHM !
365                /
366                /      SET UP AND GET THE USEFUL FEATURES
367                /
368                /
369    14611  1373         TAD (RAWDAT-1)  /SET UP AN AUTO-INDEX TO THE FEATUR
370    14612  3015         DCA AIR5        /DATA AREA.
371
372    14613  1070         TAD CH2BAS      /GET THE CH2 SDPK AND SAVE IT IN
373    14614  4772'        JMS GETDAT      /THE TABLE "RAWDAT".
374    14615  0025         SDPK
375    14616  3415         DCA I AIR5
```

/ PRODUCT QUALITY ALGORITHM                          PAL8-V10A 08/08/77 PAGE 25

```
376              /
377   14617 1067      TAD CH1BAS      /NOW GET THE CHANNEL 1 DATA.
378   14620 4771'     JMS MOVDAT
379   14621 0016      TOTPA
380   14622 0020      TOTNA
381   14623 0025      SDPK
382   14624 0031      XDMAX
383   14625 0032      MDMAX
384   14626 0000      0               /LIST TERMINATOR.
385              /
386              /    TEST THE SIZE OF THE TOTAL DEFECTIVE AREA
387              /
388   14627 7300      CLB
389   14630 1770'     TAD RAWDAT+1    /GET THE TOTAL POSITIVE AREA
390   14631 1767'     TAD RAWDAT+2    /ADD IN THE TOTAL NEGATIVE AREA
391   14632 7430      SZL             /OVERFLOW ?
392   14633 2144      ISZ PQABAD      /YES, SAY REJECT THE SHEET.
393   14634 1366      TAD (-7)        /IS THE TOTAL AREA .LT. 7 ?
394   14635 7630      SZL CLA
395   14636 2144      ISZ PQABAD      /NO, SAY REJECT THE SHEET.
396              /
397              /    NORMALIZE THE FEATURE DATA
398              /
399   14637 4765'     JMS PQNORM      /CALL THE NORMALIZER
400   14640 6630      MEN1            /(TABLE OF MEANS TO USE)
401   14641 6636      STD1            /(TABLE OF STANDARD DEVIATIONS)
402   14642 0006      6               /(NUMBER OF FEATURES TO DO)
403              /
404              /    FORM THE DISTANCE VECTORS WITH THE NORMALIZED DATA
405              /
406   14643 4764'     JMS PQAVEC      /CALL THE VECTOR SUMER.
407   14644 6660      FAC1            /(FACTOR TABLE TO USE)
408   14645 0006      6               /(NUMBER OF FEATURES)
409   14646 0006      6               /(NUMBER OF VECTORS)
410              /
411              /    FIND THE MAXIMUM DISTANCE VECTOR
412              /
413   14647 4763'     JMS PQAMAX      /CALL THE MAXIMUMER
414   14650 0003      3               /(NUMBER OF VECTORS TO DO)
415   14651 0001      1               /(FIRST VECTOR TO DO)
416              /
417              /    FIND THE MINIMUM DISTANCE VECTOR
418              /
419   14652 4762'     JMS PQAMIN      /CALL THE MINIMUMER.
420   14653 0003      3               /(NUMBER OF VECTORS TO DO)
421   14654 0004      4               /(FIRST VECTOR TO DO)
422              /
423              /    CHECK MIN/MAX VECTORS FOR A BAD SHEET
424              /
425   14655 4761'     JMS PQATST
426              /
427   14656 1144      TAD PQABAD      /IS THIS A REJECT SHEET SO FAR ?
428   14657 7640      SZA CLA
429   14660 5600 AL1XIT, JMP I AL1    /YES, ALL DONE, RETURN TO MAIN LINE.
```

/ PRODUCT QUALITY ALGORITHM                    PAL8-V10A 08/08/77  PAGE 26

```
430                /
431     14661  1360            TAD (CH1BAS)    /GO "NORMALIZE" THE SDPK'S.
432     14662  4757!           JMS PQASDN
433
434     14663  1067            TAD CH1BAS      /IS THE DEFECT WIDTH = 0 ?
435     14664  4772!           JMS GETDAT
436     14665  0031            XDMAX
437     14666  7640            SZA CLA
438     14667  5301            JMP AL1A        /NO, TRY THE OTHER ALGORITHM BRANCH
439
440     14670  1145            TAD NSDPK       /IS THE CH1 "NORM." SDPK .GE. 370 ?
441     14671  1356            TAD (-562)
442     14672  7710            SPA CLA
443     14673  5323            JMP AL1C        /NO, GO SAY GOOD SHEET.
444
445     14674  1146            TAD NSDPK2      /IS THE CH2 "NORM." SDPK .GT. 220 ?
446     14675  1355            TAD (-334)
447     14676  7750            SPA SNA CLA
448     14677  5323            JMP AL1C        /NO, MUST BE A GOOD SHEET.
449     14700  5322            JMP AL1B        /YES, GO SAY REJECT.
450
451     14701  1146    AL1A,   TAD NSDPK2      /IS THE CH2 "NORM." SDPK .GT. 220 ?
452     14702  1355            TAD (-334)
453     14703  7740            SMA SZA CLA
454     14704  5322            JMP AL1B        /YES, GO SAY BAD SHEET.
455
456     14705  1067            TAD CH1BAS      /IS THE DEFECT WIDTH .LT. 5 ?
457     14706  4772!           JMS GETDAT
458     14707  0031            XDMAX
459     14710  1354            TAD (-5)
460     14711  7710            SPA CLA
461     14712  5323            JMP AL1C        /YES, GO SAY GOOD SHEET.
462
463     14713  1145            TAD NSDPK       /IS THE CH1 "NORM." SDPK .LT. 400 ?
464     14714  1353            TAD (-620)
465     14715  7710            SPA CLA
466     14716  5323            JMP AL1C        /YES, GO SAY GOOD SHEET.
467
468     14717  1146            TAD NSDPK2      /IS THE CH2 "NORM." SDPK .LE. 200 ?
469     14720  1352            TAD (-310)
470     14721  7740            SMA SZA CLA
471     14722  2144    AL1B,   ISZ PQABAD      /NO, SAY REJECT THIS SHEET.
472     14723  5600    AL1C,   JMP I AL1       /ALL DONE, RETURN TO THE MAIN LINE.
```

/ PRODUCT QUALITY ALGORITHM                    PAL8-V10A 08/08/77  PAGE 27

```
473                /
474
475     14752  7470
476     14753  7160
477     14754  7773
478     14755  7444
479     14756  7216
480     14757  6400
481     14760  0067
482     14761  6310
483     14762  6244
```

```
484    14763   6200
485    14764   6065
486    14765   6000
487    14766   7771
488    14767   6602
489    14770   6601
490    14771   6340
491    14772   6321
492    14773   6577
493    14774   5023
494    14775   6133
495    14776   5000
496    14777   7757
497            5000         PAGE
```

/ PRODUCT QUALITY ALGORITHM                    PAL8-V10A 08/08/77  PAGE 28

```
498             /
499             /
500             /
501             /        TRY FOR A ROLL MARK DEFECT ONLY
502             /
503             /
504   15000  1140   AL1F,  TAD CH1IST    /DO WE HAVE A ROLL MARK ONLY ?
505   15001  0377          AND (7677)
506   15002  7640          SZA CLA
507   15003  5223          JMP AL1G      /NO, SOMETHING ELSE IS THERE, SAY
508                                      /REJECT THIS SHEET.
509
510   15004  1067          TAD CH1BAS    /GET THE NUMBER OF DEFECTS SEEN.
511   15005  4776'         JMS GETDAT
512   15006  0013          NUMDEF
513   15007  7450          SNA           /NUMBER OF DEFECTS ZERO ?
514   15010  5775'         JMP AL1XIT    /YES, RETURN AND SAY GOOD SHEET.
515   15011  3143          DCA PQASCR    /SAVE IT FOR DIVIDE.
516
517   15012  1067          TAD CH1BAS    /GET THE MAXIMUM MD DURATION
518   15013  4776'         JMS GETDAT
519   15014  0032          MDMAX
520
521   15015  7421          MQL
522   15016  7407          DVI           /DIVIDE "MDMAX" BY "NUMDEF".
523   15017  0143          PQASCR
524   15020  7701          ACL           /GET THE INTEGER RESULT.
525   15021  1374          TAD (-12)     /LESS THAN 10(10) ?
526   15022  7740          SMA SZA CLA
527   15023  2144   AL1G,  ISZ PQABAD    /NO, SAY REJECT THIS SHEET.
528   15024  5775'         JMP AL1XIT    /YES, SAY GOOD SHEET.
529
530   15174  7766
531   15175  4660
532   15176  6321
533   15177  7677
534           5200'        PAGE
```

/ PRODUCT QUALITY ALGORITHM                    PAL8-V10A 08/08/77  PAGE 29

```
535             /
536             /
537             /
538             /        ALGORITHM FOR CHANNEL 2 DEFECTS ONLY
539             /
```

```
540                   /
541    15200  0000  AL2,     0
542    15201  7300          CLB
543    15202  1141          TAD CH2IST       /GET THE CHANNEL 2 STATUS REGISTER.
544    15203  0377          AND (7757)       /ONLY SMALL DEFECT ?
545    15204  7640          SZA CLA
546    15205  5274          JMP AL2F         /NO, GO SAY REJECT THIS SHEET.
547
548    15206  4776'         JMS ALNUMD       /GO CHECK FOR .LE. 1 DEFECTS/SHEET.
549    15207  0001          1
550    15210  5274          JMP AL2F         /MORE THAN 1 DEFECTS PRESENT, GO SAY
551                                          /REJECT THIS SHEET.
552                   /
553                   /
554                   /     WE HAVE A DEFECT FOR THE ALGORITHM
555                   /
556                   /     FIRST CONSIDER DYE TYPE DEFECTS
557                   /
558                   /
559    15211  1070          TAD CH2BAS       /GO GET THE XDMAX FEATURE.
560    15212  4775'         JMS GETDAT
561    15213  0031          XDMAX
562    15214  7421          MQL              /SAVE IN MQ.
563    15215  7701          ACL
564    15216  1374          TAD (-4)         /IS THE DEFECT .GE. 4 CLOCKS PULSES
565    15217  7710          SPA CLA          /WIDE ?
566    15220  5234          JMP AL2A         /NO, GO LOOK AT IT ANOTHER WAY.
567
568    15221  7701          ACL
569    15222  1373          TAD (-12)        /YES, IS THE DEFECT .LE. 10(12)
570    15223  7740          SMA SZA CLA      /CLOCK PULSES WIDE ?
571    15224  5274          JMP AL2F         /NO, GO SAY REJECT THIS SHEET.
572
573    15225  1070          TAD CH2BAS       /OK, NOW LET'S LOOK AT MDMAX.
574    15226  4775'         JMS GETDAT
575    15227  0032          MDMAX
576    15230  1372          TAD (-2)         /IS THE DEFECT .LE. 2 SCANS LONG ?
577    15231  7740          SMA SZA CLA
578    15232  5274          JMP AL2F         /NO, GO SAY REJECT THIS SHEET.
579
580    15233  5600          JMP I AL2

/ PRODUCT QUALITY ALGORITHM             PALB-V10A 08/08/77  PAGE 32

581                   /
582                   /
583                   /
584                   /     WELL, NOW LOOK AT "VERY SMALL" TYPE DEFECTS
585                   /
586                   /
587    15234  7701  AL2A,   ACL              /LET'S LOOK AT XDMAX AGAIN.
588    15235  1371          TAD (-3)         /IS THE DEFECT .LE. 3 CLOCK PULSES
589    15236  7740          SMA SZA CLA      /WIDE ?
590    15237  5274          JMP AL2F         /NO, GO SAY REJECT THIS SHEET.
591
592    15240  1070          TAD CH2BAS       /NOW LOOK AT MDMAX.
593    15241  4775'         JMS GETDAT
594    15242  0032          MDMAX
595    15243  7110          CLL RAR          /IS THE DEFECT ONLY 1 SCAN LONG ?
596    15244  7640          SZA CLA
597    15245  5274          JMP AL2F         /NO, GO SAY REJECT THIS SHEET.
```

```
598
599    15246   1070    AL2B,   TAD CH2BAS       /NOW WE WILL NORMALIZE SMALL DEFECT
600    15247   4775'           JMS GETDAT       /PEAK AMPLITUDE BY AUTO-CAL.
601    15250   0022            SDAUTO
602    15251   3143            DCA PQASCR       /SAVE AUTO-CAL AS THE DIVISOR.
603    15252   1070            TAD CH2BAS
604    15253   4775'           JMS GETDAT       /NOW GET THE SDPK VALUE.
605    15254   0025            SDPK
606
607    15255   7450            SNA              /IS THE SDPK VALUE = 0 ?
608    15256   2144            ISZ PQABAD       /YES, SAY BAD SHEET.
609    15257   7421            MQL
610    15260   7405            MUY              /MULTIPLY BY 1000(10).
611    15261   5370            (1750)
612    15262   7407            DVI              /AND DIVIDE BY SDAUTO.
613    15263   0143            PQASCR
614    15264   7521            SWP              /PUT THE RESULT IN THE AC.
615    15265   7430            SZL              /TEST FOR DIVIDE OVERFLOW.
616    15266   5274            JMP AL2F         /DID OVERFLOW, SAY REJECT THE SHEET
617    15267   3143            DCA PQASCR       /SAVE THE NORMALIZED DATA.
618
619    15270   1367            TAD (-1440)      /IS IT .LE. 800(10)
620    15271   7740            SMA SZA CLA
621    15272   5274            JMP AL2F         /NO-SAY REJECT THIS SHEET
622    15273   5600            JMP I AL2

/ PRODUCT QUALITY ALGORITHM                    PAL8-V10A 08/08/77  PAGE 31

623                    /
624    15274   2144    AL2F,   ISZ PQABAD       /NO, SAY REJECT THIS SHEET.
625    15275   5600            JMP I AL2        /ALL DONE FOR THIS ALGORITHM, RETUR
626
627    15367   6340
628    15370   1750
629    15371   7775
630    15372   7776
631    15373   7766
632    15374   7774
633    15375   6321
634    15376   6133
635    15377   7757
636            5400            PAGE

/ PRODUCT QUALITY ALGORITHM                    PAL8-V10A 08/08/77  PAGE 32

637                    /
638                    /
639                    /
640                    /       ALGORITHM FOR CHANNEL 3 DEFECTS ONLY
641                    /
642                    /
643    15400   0000    AL3,    0
644    15401   7300            CLB
645    15402   1142            TAD CH3IST       /GET THE CHANNEL 3 STATUS REGISTER.
646    15403   0377            AND (7757)       /ONLY SMALL DEFECT ?
647    15404   7640            SZA CLA
648    15405   5776'           JMP AL3F         /NO, TRY FOR ROLL MARK.
649                    /
650                    /
651                    /
652
```

```
653   15406   4775'         JMS ALNUM0      /GO CHECK FOR ONLY 1 DEFECT/SHEET.
654   15407   0001          1
655   15410   5774'         JMP AL3G        /MORE THAN 1 DEFECT PRESENT, GO SA'
656                                         /REJECT THIS SHEET.
657                  /
658                  /
659                  /       WE HAVE A SHEET FOR THE ALGORITHM !
660                  /
661                  /       SET UP AND GET THE USEFUL FEATURES
662                  /
663                  /
664   15411   1373          TAD (RAWDAT-1)  /SET UP AN AUTO-INDEX TO THE FEATUR
665   15412   3015          DCA AIR5        /DATA AREA.
666
667   15413   1070          TAD CH2BAS      /GET THE CH2 SDPK AND SAVE IT IN
668   15414   4772'         JMS GETDAT      /THE TABLE "RAWDAT".
669   15415   0025          SDPK
670   15416   3415          DCA I AIR5
```

/ PRODUCT QUALITY ALGORITHM                          PAL8-V10A 08/28/77  PAGE 33

```
671                  /
672   15417   1071          TAD CH3BAS      /NOW GET THE CHANNEL 3 DATA.
673   15420   4771'         JMS MOVDAT
674   15421   0016          TOTPA
675   15422   0020          TOTNA
676   15423   0025          SDPK
677   15424   0031          XDMAX
678   15425   0032          MDMAX
679   15426   0000          0               /LIST TERMINATOR.
680                  /
681                  /       TEST THE SIZE OF THE TOTAL DEFECTIVE AREA
682                  /
683   15427   7300          CLB
684   15430   1770'         TAD RAWDAT+1    /GET THE TOTAL POSITIVE AREA
685   15431   1767'         TAD RAWDAT+2    /ADD IN THE TOTLA NEGATIVE AREA
686   15432   7430          SZL             /OVERFLOW ?
687   15433   2144          ISZ PQABAD      /YES, SAY REJECT THE SHEET.
688   15434   1366          TAD (-7)        /IS THE TOTAL AREA .LT. 7 ?
689   15435   7630          SZL CLA
690   15436   2144          ISZ PQABAD      /NO, SAY REJECT THE SHEET.
691                  /
692                  /       NORMALIZE THE FEATURE DATA
693                  /
694   15437   4765'         JMS PQNORM      /CALL THE NORMALIZER
695   15440   0644          MEN3            /(TABLE OF MEANS TO USE)
696   15441   6652          STD3            /(TABLE OF STANDARD DEVIATIONS)
697   15442   0006          6               /(NUMBER OF FEATURES TO DO)
698                  /
699                  /       FORM THE DISTANCE VECTORS WITH THE NORMALIZED DATA
700                  /
701   15443   4764'         JMS PQAVEC      /CALL THE VECTOR SUMER.
702   15444   6724          FAC3            /(FACTOR TABLE TO USE)
703   15445   0006          6               /(NUMBER OF FEATURES)
704   15446   0006          6               /(NUMBER OF VECTORS)
705                  /
706                  /       FIND THE MAXIMUM DISTANCE VECTOR
707                  /
```

```
708  15447  4763'          JMS PQAMAX        /CALL THE MAXIMUMER
709  15450  0003           3                 /(NUMBER OF VECTORS TO DC)
710  15451  0001           1                 /(FIRST VECTOR TO DO)
711                /
712                /       FIND THE MINIMUM DISTANCE VECTOR
713                /
714  15452  4762'          JMS PQAMIN        /CALL THE MINIMUMER.
715  15453  0003           3                 /(NUMBER OF VECTORS TO DC)
716  15454  0004           4                 /(FIRST VECTOR TO DO)
717
718                /
719                /       CHECK MIN/MAX VECTORS FOR A BAD SHEET
720                /
721  15455  4761'          JMS PQATST
722                /
723  15456  1144           TAD PQABAD        /IS THIS A REJECT SHEET SO FAR ?
724  15457  7640           SZA CLA
725  15460  5600  AL3XIT,  JMP I AL3         /YES, ALL DONE, RETURN TO MAIN LINE.

/ PRODUCT QUALITY ALGORITHM                  PAL8-V10A 08/08/77  PAGE 34

726
727  15461  1360           TAD (CH3BAS)      /GO "NORMALIZE" THE SDPK'S.
728  15462  4757'          JMS PQASDN
729
730  15463  1071           TAD CH3BAS        /IS THE DEFECT WIDTH = 0 ?
731  15464  4772'          JMS GETDAT
732  15465  0031           XDMAX
733  15466  7640           SZA CLA
734  15467  5301           JMP AL3A          /NO, TRY THE OTHER ALGORITHM BRANCH
735
736  15470  1145           TAD NSDPK         /IS THE CH3 "NORM." SDPK .GE. 370 ?
737  15471  1356           TAD (-562)
738  15472  7710           SPA CLA
739  15473  5323           JMP AL3C          /NO, GO SAY GOOD SHEET.
740
741  15474  1146           TAD NSDPK2        /IS THE CH2 "NORM." SDPK .GT. 220 ?
742  15475  1355           TAD (-334)
743  15476  7750           SPA SNA CLA
744  15477  5323           JMP AL3C          /NO, MUST BE A GOOD SHEET.
745  15500  5322           JMP AL3B          /YES, GO SAY REJECT.
746
747  15501  1146  AL3A,    TAD NSDPK2        /IS THE CH2 "NORM." SDPK .GT. 220 ?
748  15502  1355           TAD (-334)
749  15503  7740           SMA SZA CLA
750  15504  5322           JMP AL3B          /YES, GO SAY BAD SHEET.
751
752  15505  1071           TAD CH3BAS        /IS THE DEFECT WIDTH .LT. 5 ?
753  15506  4772'          JMS GETDAT
754  15507  0031           XDMAX
755  15510  1354           TAD (-5)
756  15511  7710           SPA CLA
757  15512  5323           JMP AL3C          /YES, GO SAY GOOD SHEET.
758
759  15513  1145           TAD NSDPK         /IS THE CH3 "NORM." SDPK .LT. 400 ?
760  15514  1353           TAD (-620)
761  15515  7710           SPA CLA
762  15516  5323           JMP AL3C          /YES, GO SAY GOOD SHEET.
763
```

```
764  15517  1146        TAD NSDPK2      /IS THE CH2 "NORM." SDPK .LE. 200 ?
765  15520  1352        TAD (-310)
766  15521  7740        SMA SZA CLA
767  15522  2144  AL3B, ISZ PQABAD      /NO, SAY REJECT THIS SHEET.
768  15523  5600  AL3C, JMP I AL3       /ALL DONE, RETURN TO THE MAIN LINE.
```

/ PRODUCT QUALITY ALGORITHM                 PAL8-V10A 08/08/77  PAGE 35

```
769                /
770
771  15552  7470
772  15553  7160
773  15554  7773
774  15555  7444
775  15556  7216
776  15557  6400
777  15560  0071
778  15561  6310
779  15562  6244
780  15563  6200
781  15564  6065
782  15565  6000
783  15566  7771
784  15567  6502
785  15570  6601
786  15571  6340
787  15572  6321
788  15573  6577
789  15574  5623
790  15575  6133
791  15576  5600
792  15577  7757
793         5600        PAGE
```

/ PRODUCT QUALITY ALGORITHM                 PAL8-V10A 08/08/77  PAGE 36

```
794                /
795                /
796                /
797                /   TRY FOR A ROLL MARK DEFECT ONLY
798                /
799                /
800  15600  1142  AL3F, TAD CH3IST      /DO WE HAVE A ROLL MARK ONLY ?
801  15601  0377        AND (7677)
802  15602  7640        SZA CLA
803  15603  5223        JMP AL3G        /NO, SOMETHING ELSE IS THERE, SAY
804                                     /REJECT THIS SHEET.
805
806  15604  1071        TAD CH3BAS      /GET THE NUMBER OF DEFECTS SEEN.
807  15605  4776'       JMS GETDAT
808  15606  0013        NUMDEF
809  15607  7450        SNA             /NUMBER OF DEFECTS ZERO ?
810  15610  5775'       JMP AL3XIT      /YES, RETURN AND SAY GOOD SHEET.
811  15611  3143        DCA PQASCR      /SAVE IT FOR DIVIDE.
812
813  15612  1071        TAD CH3BAS      /GET THE MAXIMUM MD DURATION
814  15613  4776'       JMS GETDAT
815  15614  0032        MDMAX
816
```

```
817  15615  7421         MQL
818  15616  7407         DVI           /DIVIDE "MDMAX" BY "NUMDEF".
819  15617  6143         PQASCR
820  15620  7701         ACL           /GET THE INTEGER RESULT.
821  15621  1374         TAD (-12)     /LESS THAN 10(10) ?
822  15622  7740         SMA SZA CLA
823  15623  2144  AL3G,  ISZ PQABAD    /NO, SAY REJECT THIS SHEET.
824  15624  5775!        JMP AL3XIT    /YES, SAY GOOD SHEET.
825
826  15774  7766
827  15775  5460
828  15776  6321
829  15777  7677
830         6000!        PAGE
```

/ PRODUCT QUALITY ALGORITHM                    PAL8-V10A 08/08/77  PAGE 37

```
831         /
832         /
833         /
834         /   SUBROUTINE TO NORMALIZE FEATURE DATA.
835         /
836         /   NORMALIZE THE FEATURE DATA IN "RAWDAT". THE CALLING
837         /   ARGUMENTS SPECIFY THE TABLES TO USE FOR MEAN AND
838         /   STANDARD DEVIATION. THE NORMALIZED DATA IS STORED IN
839         /   THE "NORMDT" AREA.
840         /
841         /   THE NORMALIZING EQUATION IS:
842         /
843         /       NORMDT(I) = 100(10)*[ FEATURE(I)-MEAN(I) ]
844         /                   --------------------------------
845         /
846         /                         STANDARD DEVIATION(I)
847         /
848         /   CALLING SEQUENCE:
849         /
850         /           JMS PQNORM
851         /              ADDRESS OF THE MEAN TABLE
852         /              ADDRESS OF THE STANDARD DEVIATION TABLE
853         /              NUMBER OF FEATURES TO PROCESS
854         /
855         /
856  16000  0000  PQNORM, 0
857  16001  7340         CLB CMA
858  16002  1600         TAD I PQNORM   /GET THE ADDRESS OF THE TABLE OF
859  16003  2200         ISZ PQNORM     /MEANS TO USE.
860  16004  3015         DCA AIR5
861  16005  1600         TAD I PQNORM   /GET THE ADDRESS OF THE TABLE OF
862  16006  2200         ISZ PQNORM     /STANDARD DEVIATIONS TO USE.
863  16007  3236         DCA PQAN2
864
865  16010  1600         TAD I PQNORM   /GET THE NUMBER OF FEATURES TO
866  16011  2200         ISZ PQNORM     /NORMALIZE
867  16012  7041         CIA
868  16013  3143         DCA PQASCR
869  16014  1377         TAD (RAWDAT)   /SET ADDRESS POINTER TO THE FEATURE
870  16015  3263         DCA PQANA      /DATA AREA.
871  16016  1376         TAD (NORMDT-1) /SET UP AN AUTO-INDEX TO THE
872  16017  3016         DCA AIR6       /NORMALIZED DATA AREA.
873
```

```
 874   16020  1415   PQAN1,  TAD I AIR5       /GET THE MEAN FOR THIS FEATURE,
 875   16021  7041           CIA              /MAKE IT NEGATIVE (TO SUBTRACT)
 876   16022  1663           TAD I PQANA      /ADD IN THE CURRENT FEATURE DATA,
 877   16023  3264           DCA PQANB        /SAVE THE NUMBER FOR IT'S SIGN.
 878   16024  1264           TAD PQANB
 879   16025  7510           SPA              /IS THE RESULT POSITIVE ?
 880   16026  7041           CIA              /NO, MAKE IT POSITIVE FOR DIVIDE !
 881   16027  7421           MQL
```

/ PRODUCT QUALITY ALGORITHM                PAL8-V10A 08/08/77  PAGE 38

```
 882                   /
 883   16030  1663            TAD I PQANA      /GET THE FEATURE AGAIN, .GT. 4000?
 884   16031  7710            SPA CLA
 885   16032  5260            JMP PQAN3        /YES, QUIT AND SAY REJECT SHEET.
 886
 887   16033  7405            MUY              /MULTIPLY BY 100(10).
 888   16034  0175            (144)
 889   16035  7407            DVI              /DIVIDE BY THE STANDARD DEVIATION.
 890   16036  0000   PQAN2,   0
 891   16037  7430            SZL              /CHECK FOR DIVIDE OVERFLOW.
 892   16040  7621            CAM              /DID OVERFLOW, SET RESULT TO ZERO.
 893
 894   16041  7701            ACL              /GET THE INTEGER OF THE RESULT.
 895   16042  1374            TAD (-3410)      /IS IT GREATER THAN 1800(10) ?
 896   16043  7700            SMA CLA
 897   16044  5260            JMP PQAN3        /YES, QUIT AND SAY REJECT SHEET.
 898
 899   16045  1264            TAD PQANB        /GET THE SIGN OF THE NUMBER BEFORE
 900   16046  7104            CLL RAL          /THE DIVISION.
 901   16047  7701            ACL              /GET THE QUOTIENT.
 902   16050  7430            SZL              /WAS IT NEGATIVE ?
 903   16051  7041            CIA              /YES, MAKE IT NEGATIVE AGAIN.
 904   16052  3416            DCA I AIR6       /STORE NORMALIZE FEATURE IN TABLE.
 905
 906   16053  2263            ISZ PQANA        /INCREMENT THE POINTERS.
 907   16054  2236            ISZ PQAN2
 908   16055  2143            ISZ PQASCR       /FINISHED ALL THE FEATURES ?
 909   16056  5220            JMP PQAN1        /NO, DO ANOTHER.
 910   16057  5600            JMP I PQNORM     /AND RETURN.
 911
 912   16060  7301   PQAN3,   CLB IAC          /SET "PQABAD" TO REJECT THIS SHEET.
 913   16061  3144            DCA PQABAD
 914   16062  5600            JMP I PQNORM     /AND RETURN.
 915
 916
 917   16063  0000   PQANA,   0                /LOCAL TEMPORARIES.
 918   16064  0000   PQANB,   0
```

/ PRODUCT QUALITY ALGORITHM                PAL8-V10A 08/08/77  PAGE 39

```
 919             /
 920             /
 921             /
 922             /
 923             /         SUBROUTINE TO EVALUATE DISTANCE VECTORS.
 924             /
 925             /         THE DISTANCE VECTORS ARE FORMED BY SUMMING THE
 926             /         NORMALIZED FEATURES WITH THE VECTOR FACTORS. THE
 927             /         RESULTANT SUMS ARE STORED IN THE TABLE
 928             /         "VECTBL".
```

```
929                /        THE SUMMATION IS:
930                /
931                /                        N
932                /        VECTBL(I) = SUM ( ABS( NORMDT(J)+FACTOR(I,J) ) )
933                /                       J=1
934                /
935                /
936                /        CALLING SEQUENCE:
937                /
938                /                JMS PQAVEC
939                /                    ADDRESS OF THE VECTOR FACTORS
940                /                    NUMBER OF FEATURES TO SUM
941                /                    NUMBER OF VECTOR TO SUM
942                /
943                /
944    16065  0000   PQAVEC, 0
945    16066  7340           CLA CMA
946    16067  1665           TAD I PQAVEC      /GET THE ADDRESS OF THE TABLE OF
947    16070  2265           ISZ PQAVEC        /VECTOR FACTORS TO USE.
948    16071  3015           DCA AIR5
949    16072  1665           TAD I PQAVEC      /GET THE NUMBER OF FEATURES TO DO.
950    16073  2265           ISZ PQAVEC
951    16074  7041           CIA
952    16075  3332           DCA PQAVB
953    16076  1373           TAD (VECTBL-1)    /SET UP AUTO-INDEX TO VECTOR TABLE.
954    16077  3017           DCA AIR7
955
956    16100  1376   PQAV1,  TAD (NORMDT-1)    /SET UP AUTO-INDEX TO THE NORMALIZE
957    16101  3016           DCA AIR6          /FEATURE DATA LIST.
958    16102  1665           TAD I PQAVEC      /LOOP COUNT OF NUMBER OF FACTORS TO
959    16103  7041           CIA               /SUM PER FEATURE.
960    16104  3143           DCA PQASCR
961
962    16105  3331   PQAV2,  DCA PQAVA
963    16106  1415           TAD I AIR5        /GET THE VECTOR FACTOR,
964    16107  7041           CIA               /NEGATE IT (FOR SUBTRACT), AND
965    16110  1416           TAD I AIR6        /ADD IN THE FEATURE VALUE,
966    16111  7510           SPA
967    16112  7041           CIA               /FORCE THE ABSOLUTE VALUE,
968    16113  7100           CLL               /(CLEAR THE LINK FOR OVERFLOW TEST)
969    16114  1331           TAD PQAVA         /AND ACCUMULATE THE VECTOR VALUE.
/ PRODUCT QUALITY ALGORITHM              PAL8-V10A 08/08/77   PAGE 40
970                /
971    16115  7420           SNL               /DID THE VECTOR OVERFLOW ?
972    16116  5322           JMP PQAV3         /NO, GO ON.
973
974    16117  7301           CLA IAC           /YES, SET THE MARK TO REJECT THIS
975    16120  3144           DCA PQABAD        / SHEET.
976    16121  5327           JMP PQAV4         /AND EXIT.
977
978    16122  2143   PQAV3,  ISZ PQASCR        /FINISHED ?
979    16123  5305           JMP PQAV2         /NO, GO AROUND AGAIN.
980    16124  3417           DCA I AIR7        /YES, STORE VECTOR IN TABLE.
981    16125  2332           ISZ PQAVB         /FINISHED ALL FEATURES ?
982    16126  5300           JMP PQAV1         /NO, TRY ANOTHER.
983    16127  2265   PQAV4,  ISZ PQAVEC        /INCREMENT THE RETURN ADDRESS.
984    16130  5665           JMP I PQAVEC      /RETURN.
985
986
987    16131  0000   PQAVA,  0                 /LOCAL TEMPORARIES.
988    16132  0000   PQAVB,  0
```

/ PRODUCT QUALITY ALGORITHM                               PAL8-V10A 08/08/77  PAGE 41

```
989        /
990        /
991        /
992        /        SUBROUTINE TO CHECK THE NUMBER OF DEFECTS
993        /        SEEN BY EACH CHANNEL.
994        /
995        /
996        /        ACCUMULATE THE TOTAL NUMBER OF DEFECTS SEEN ON
997        /        THIS SHEET, AND COMPARE THIS TOTAL TO THE NUMBER
998        /        THE CALLER WILL ALLOW. IF THE NUMBER OF DEFECTS
999        /        IS LESS THAN OR EQUAL TO THE ALLOWED NUMBER,
1000       /        INCREMENT THE RETURN ADDRESS TO SAY WE CAN RUN
1001       /        THIS SHEET THROUGH THE ALGORITHM (TAKE THE
1002       /        SECOND EXIT). FOR MORE DEFECTS THAN ALLOWED,
1003       /        TAKE THE FIRST EXIT TO SAY BAD SHEET.
1004       /
1005       /
1006       /        CALLING SEQUENCE:
1007       /
1008       /                JMS ALNUMD
1009       /                NUMBER OF DEFECTS ALLOWED ON THIS SHEET
1010       /
1011       /
1012  16133  0000   ALNUMD, 0
1013  16134  7300           CLB
1014  16135  1067           TAD CH1BAS
1015  16136  4772'          JMS GETDAT      /FIRST GET THE NUMBER OF CH1 DEFECTS
1016  16137  0013           NUMDEF
1017  16140  3360           DCA ALNUA       /SAVE THE NUMBER OF DEFECTS.
1018
1019  16141  1070           TAD CH2BAS      /NOW CH2
1020  16142  4772'          JMS GETDAT
1021  16143  0013           NUMDEF
1022  16144  1360           TAD ALNUA
1023  16145  3360           DCA ALNUA       /ACCUMULATE THE NUMBER OF DEFECTS.
1024
1025  16146  1071           TAD CH3BAS      /AND NOW ADD IN CH3
1026  16147  4772'          JMS GETDAT
1027  16150  0013           NUMDEF
1028
1029  16151  1360           TAD ALNUA       /ADD IN THE OTHER CHANNELS.
1030  16152  7041           CIA
1031  16153  1733           TAD I ALNUMD    /ADD IN THE CALLER'S ARGUMENT.
1032  16154  2333           ISZ ALNUMD      /INCREMENT PAST THE ARGUMENT.
1033
1034  16155  7700           SMA CLA         /TOO MANY DEFECTS PRESENT ?
1035  16156  2333           ISZ ALNUMD      /NO, INCREMENT THE RETURN ADDRESS
1036                                        /TO SAY "ALGORITHMABLE" SHEET.
1037  16157  5733   ALN1,   JMP I ALNUMD    /RETURN.
1038
1039  16160  0000   ALNUA,  0
```

/ PRODUCT QUALITY ALGORITHM                               PAL8-V10A 08/08/77  PAGE 42

```
1040       /
1041
1042  16172  6321
1043  16173  6617
1044  16174  4370
1045  16175  0144
1046  16176  6607
1047  16177  6600
1048         6200
```

/ PRODUCT QUALITY ALGORITHM                              PAL8-V10A 08/08/77   PAGE 43

```
1049
1050            /
1051            /
1052            /          SUBROUTINE TO FIND THE MAXIMUM OF THE DISTANCE
1053            /          VECTORS IN THE VECTOR TABLE, VECTBL.
1054            /
1055            /          RETURN WITH THE VALUE OF THE MAXIMUM VECTOR IN
1056            /          "MAXVAL", AND THE VECTOR INDEX IN "MAXDEX".
1057            /
1058            /
1059            /          CALLING SEQUENCE:
1060            /
1061            /               JMS PQAMAX
1062            /                  NUMBER OF VECTORS TO DO
1063            /                  FIRST VECTOR TO DO
1064            /
1065            /
1066   16200  0000    PQAMAX, 0
1067   16201  7300            CLB
1068   16202  1600            TAD I PQAMAX        /SAVE THE NUMBER OF VECTORS TO DO.
1069   16203  3241            DCA PQAMAB
1070   16204  7340            CLB CMA             /LOOP COUNTER = FEATURES -1.
1071   16205  1600            TAD I PQAMAX
1072   16206  2200            ISZ PQAMAX
1073   16207  7041            CIA
1074   16210  3143            DCA PQASCR
1075
1076   16211  1600            TAD I PQAMAX        /GET THE INDEX OF THE VECTOR TO
1077   16212  3243            DCA MAXDEX          /START ON.
1078
1079   16213  1377            TAD (VECTBL-1)      /SET UP A POINTER TO THE VECTOR
1080   16214  1243            TAD MAXDEX          /TABLE.
1081   16215  3240            DCA PQAMAA
1082   16216  1640            TAD I PQAMAA        /USE THE FIRST VECTOR AS THE INITIA
1083   16217  3242            DCA MAXVAL          /MAXIMUM VALUE.
1084
1085   16220  2240    PQAMA1, ISZ PQAMAA          /INCREMENT THE VECTOR POINTER.
1086   16221  1242            TAD MAXVAL          /GET THE PREVIOUS MAXIMUM VALUE AND
1087   16222  7141            CLL CIA
1088   16223  1640            TAD I PQAMAA        /SUBTRACT FROM NEW VECTOR.
1089   16224  7620            SNL CLA             /IS THE NEW VALUE NOW THE MAXIMUM ?
1090   16225  5234            JMP PQAMA2          /NO, GO ON.
1091
1092   16226  1640            TAD I PQAMAA        /YES, UPDATE THE MAXIMUM VALUE.
1093   16227  3242            DCA MAXVAL
1094   16230  1143            TAD PQASCR          /UPDATE THE VECTOR INDEX.
1095   16231  1241            TAD PQAMAB          /MODULO THE NUMBER OF VECTORS,
1096   16232  1600            TAD I PQAMAX        /PLUS THE FIRST VECTOR OFFSET.
1097   16233  3243            DCA MAXDEX
```

/ PRODUCT QUALITY ALGORITHM                              PAL8-V10A 08/08/77   PAGE 44

```
1098            /
1099   16234  2143    PQAMA2, ISZ PQASCR          /FINISHED WITH ALL THE VECTORS ?
1100   16235  5220            JMP PQAMA1          /NO, TRY AGAIN.
1101   16236  2200            ISZ PQAMAX          /INCRMENT THE RETURN ADDRESS.
1102   16237  5600            JMP I PQAMAX        /RETURN.
1103
1104   16240  0000    PQAMAA, 0                   /LOCAL TEMPORARYS
1105   16241  0000    PQAMAB, 0
1106   16242  0000    MAXVAL, 0
1107   16243  0000    MAXDEX, 0
```

```
/ PRODUCT QUALITY ALGORITHM                           PAL8-V10A 08/08/77   PAGE 45

1108
1109                /
1110                /
1111                /       SUBROUTINE TO FIND THE MINIMUM OF THE DISTANCE
1112                /       VECTORS IN THE VECTOR TABLE, VECTBL.
1113                /
1114                /       RETURN WITH THE VALUE OF THE MINIMUM VECTOR IN
1115                /       "MINVAL", AND THE VECTOR INDEX IN "MINDEX".
1116                /
1117                /
1118                /       CALLING SEQUENCE:
1119                /
1120                /               JMS PQAMIN
1121                /               NUMBER OF VECTORS TO DO
1122                /               FIRST VECTOR TO DO
1123                /
1124                /
1125     16244  0000   PQAMIN, 0
1126     16245  7300           CLB
1127     16246  1644           TAD I PQAMIN    /SAVE THE NUMBER OF VECTORS TO DO.
1128     16247  3305           DCA PQAMIB
1129     16250  7340           CLB CMA         /LOOP COUNTER = FEATURES -1.
1130     16251  1644           TAD I PQAMIN
1131     16252  2244           ISZ PQAMIN
1132     16253  7041           CIA
1133     16254  3143           DCA PQASCR
1134
1135     16255  1644           TAD I PQAMIN    /GET THE INDEX OF THE VECTOR TO
1136     16256  3307           DCA MINDEX      /START ON.
1137
1138     16257  1377           TAD (VECTBL-1)  /SET UP A POINTER TO THE VECTOR
1139     16260  1307           TAD MINDEX      /TABLE.
1140     16261  3304           DCA PQAMIA
1141     16262  1704           TAD I PQAMIA    /USE THE FIRST VECTOR AS THE INITIAL
1142     16263  3306           DCA MINVAL      /MINIMUM VALUE.
1143
1144     16264  2304   PQAMI1, ISZ PQAMIA      /INCREMENT THE VECTOR POINTER.
1145     16265  1306           TAD MINVAL      /GET THE PREVIOUS MINIMUM VALUE AND
1146     16266  7141           CLL CIA
1147     16267  1704           TAD I PQAMIA    /SUBTRACT FROM NEW VECTOR.
1148     16270  7630           SZL CLA         /IS THE NEW VALUE NOW THE MINIMUM ?
1149     16271  5300           JMP PQAMI2      /NO, GO ON.
1150
1151     16272  1704           TAD I PQAMIA    /YES, UPDATE THE MINIMUM VALUE.
1152     16273  3306           DCA MINVAL
1153     16274  1143           TAD PQASCR      /UPDATE THE VECTOR INDEX.
1154     16275  1305           TAD PQAMIB      /MODULO THE NUMBER OF VECTORS,
1155     16276  1644           TAD I PQAMIN    /PLUS THE FIRST VECTOR OFFSET.
1156     16277  3307           DCA MINDEX

/ PRODUCT QUALITY ALGORITHM                           PAL8-V10A 08/08/77   PAGE 46

1157                /
1158     16300  2143   PQAMI2, ISZ PQASCR      /FINISHED WITH ALL THE VECTORS ?
1159     16301  5264           JMP PQAMI1      /NO, TRY AGAIN.
1160     16302  2244           ISZ PQAMIN      /INCREMENT THE RETURN ADDRESS.
1161     16303  5644           JMP I PQAMIN    /RETURN.
1162
1163     16304  0000   PQAMIA, 0               /LOCAL TEMPORARYS
1164     16305  0000   PQAMIB, 0
1165     16306  0000   MINVAL, 0
1166     16307  0000   MINDEX, 0
```

/ PRODUCT QUALITY ALGORITHM                    PAL8-V18A 08/08/77  PAGE 47

```
1167
1168                /
1169                /           CHECK THE MIN/MAX VECTOR VALUES TO DETERMINE THE
1170                /           SHEET QUALITY.
1171                /
1172                /           COME HERE AFTER COMPUTING THE MAXIMUM VALUE FOR THE
1173                /           GOOD VECTORS (1-3) AND THE MINIMUM OF THE REJECT
1174                /           VECTORS (4-6). FOR A GOOD SHEET, THE MAXIMUM VALUE
1175                /           MUST BE LESS THAN THE MINIMUM VALUE. IF THE VALUES
1176                /           ARE EQUAL, THE SHEET IS A REJECT.
1177                /
1178                /
1179  16310  0000   PQATST, 0
1180  16311  7301           CLB IAC        /(IAC MAKES "EQUAL" A REJECT.)
1181  16312  1242           TAD MAXVAL     /GET THE MAXIMUM VALUE AND
1182  16313  7141           CLL CIA
1183  16314  1306           TAD MINVAL     /COMPARE TO THE MINIMUM VALUE
1184  16315  7620           SNL CLA        /DOES MAX. EXCEED MIN. ?
1185  16316  2144           ISZ PQABAD     /YES, SET THE FLAG TO SAY BAD SHEET.
1186  16317  5710           JMP I PQATST   /RETURN.
1187                /
1188                /
1189                /
1190                /           SUBROUTINE TO GET A WORD OF DATA OUT OF THE
1191                /           SHEET DATA TABLE. THE BASE ADDRESS IS IN THE
1192                /           ACCUMULATOR WHEN CALLED, AND THE DATA OFFSET
1193                /           FOLLOWS THE CALL. THE DATA FROM THE DESIRED
1194                /           LOCATION IS RETURNED IN THE ACCUMULATOR.
1195                /
1196                /
1197  16320  0000           0
1198  16321  0000   GETDAT, 0
1199  16322  1721           TAD I GETDAT   /ADD IN THE OFFSET.
1200  16323  2321           ISZ GETDAT
1201  16324  3320           DCA GETDAT-1   /SAVE FOR INDIRECT ADDRESS.
1202  16325  6221           CDF DATFLD     /SET THE DATA FIELD TO THE BUFFER.
1203  16326  1720           TAD I GETDAT-1 /GET THE DESIRED DATA WORD.
1204  16327  6211           CDF CUR        /RESET THE DATA FIELD TO HERE.
1205  16330  5721           JMP I GETDAT   /RETURN.
1206                /
1207                /
1208                /           SUBROUTINE TO PUT DATA BACK IN THE SHEET DATA
1209                /           TABLE AT THE ADDRESS LEFT BY "GETDAT". "GETDAT"
1210                /           COMPUTES THE DATA ADDRESS FOR "PUTDAT".
1211                /
1212                /
1213  16331  0000   PUTDAT, 0
1214  16332  6221           CDF DATFLD     /SET THE DATA FIELD TO THE BUFFER.
1215  16333  3720           DCA I GETDAT-1 /PUT THE DATA BACK IN THE BUFFER.
1216  16334  6211           CDF CUR        /RESET THE DATA FIELD TO HERE.
1217  16335  7300           CLB
1218  16336  5731           JMP I PUTDAT   /AND RETURN.
```

/ PRODUCT QUALITY ALGORITHM                    PAL8-V18A 08/08/77  PAGE 48

```
1219                /
1220                /
1221                /
```

```
1222                    /       SUBROUTINE TO GET A LIST OF FEATURE DATA AND STORE
1223                    /       IT FOR THE USER VIA AIR5. THIS SUBROUTINE CAN ONLY
1224                    /       GET DATA FOR ONE CHANNEL AT A TIME. THE CHANNEL
1225                    /       BASE ADDRESS IS IN THE ACCUMULATOR WHEN CALLED,
1226                    /       AND A LIST OF THE DESIRED FEATURES (DATA OFFSETS)
1227                    /       FOLLOWS THE CALL. A ZERO WORD TERMINATES THE LIST.
1228                    /       THIS SUBROUTINE CALLS "GETDAT" TO FETCH THE DATA.
1229                    /       NOTE: THE USER MUST HAVE PRESET AIR5 BEFORE COMING
1230                    /       HERE !!
1231                    /
1232                    /
1233    16337   0000            0
1234    16340   0000    MOVDAT, 0
1235    16341   3337            DCA MOVDAT-1    /SAVE THE BASE ADDRESS.
1236    16342   1740    MOVD1,  TAD I MOVDAT    /GET THE NEXT FEATURE ARGUMENT.
1237    16343   2340            ISZ MOVDAT
1238    16344   7450            SNA             /ZERO IS CALL TERMINATOR.
1239    16345   5740            JMP I MOVDAT    /'TIS ZERO, ALL DONE, RETURN.
1240    16346   3351            DCA .+3         /SAVE OFFSET FOR "GETDAT".
1241    16347   1337            TAD MOVDAT-1    /GET THE BASE ADDRESS IN THE AC,
1242    16350   4321            JMS GETDAT      /AND CALL "GETDAT".
1243    16351   0000            0               /(WILL BE FEATURE OFFSET ADDRESS)
1244    16352   3415            DCA I AIR5      /SAVE THE DATA FOR THE USER.
1245    16353   5342            JMP MOVD1       /LET'S DO IT AGAIN.
1246
1247    16377   6617
1248            6400            PAGE
```

/ PRODUCT QUALITY ALGORITHM              PAL8-V10A 08/08/77  PAGE 45

```
1249                    /
1250                    /
1251                    /
1252                    /       SUBROUTINE TO SCALE (OR NORMALIZE) THE SDPK (SMALL
1253                    /       DEFECT PEAK AMPLITUDE) BY THE SDAUTO (SMALL DEFECT
1254                    /       AUTOCAL) VALUE FOR A REFLECTION CHANNEL AND CHANNEL
1255                    /       TWO. THE ADDRESS OF THE REFLECTION CHANNEL BASE
1256                    /       POINTER IS IN THE ACCUMULATOR ON CALL. THE RESULTS
1257                    /       ARE STORED IN "NSDPK" AND "NSDPK2" FOR THE REFLECT-
1258                    /       ION CHANNEL AND CHANNEL TWO RESPECTIVELY.
1259                    /
1260                    /       THE  C U R R E N T  NORMALIZING EQUATION IS:
1261                    /
1262                    /       NSDPK = SDPK + SDPK * 500(10)
1263                    /                     ---------------
1264                    /                          SDAUTO
1265                    /
1266                    /
1267    16400   0000    PQASDN, 0
1268    16401   4207            JMS PQAS1       /GO SCALE THE REFLECTION CHANNEL
1269    16402   3145            DCA NSDPK       /SAVE THE SCALED RESULT.
1270    16403   1377            TAD (CH2BAS)    /NOW DO THE SAME FOR CHANNEL TWO.
1271    16404   4207            JMS PQAS1
1272    16405   3146            DCA NSDPK2      /SAVE THE CHANNEL 2 RESULT.
1273    16406   5600            JMP I PQASDN    /AND RETURN.
1274
1275    16407   0000    PQAS1,  0
1276    16410   3143            DCA PQASCR      /SAVE THE ADDRESS OF THE CHANNEL
1277                                            /BASE POINTER.
1278    16411   1543            TAD I PQASCR    /GET THE CHANNEL BASE POINTER AND
1279    16412   4776            JMS GETDAT      /GET THE SDAUTO FOR THIS CHANNEL.
1280    16413   0022            SDAUTO
```

```
1281   16414  3236           DCA PQAS2        /SAVE IT AS THE DIVISOR.
1282   16415  1543           TAD I PQASCR     /GET THE BASE POINTER AGAIN AND
1283   16416  4776'          JMS GETDAT       /NOW GET THE SDPK VALUE.
1284   16417  0025           SDPK
1285
1286   16420  3237           DCA PQAS3        /SAVE ORIGINAL SDPK FOR LATER.
1287   16421  1237           TAD PQAS3
1288
1289   16422  7450           SNA              /IS THE SDPK VALUE = 0 ?
1290   16423  2144           ISZ PQABAD       /YES, SAY BAD SHEET.
1291   16424  7421           MQL
1292   16425  7405           MUY              /MULTIPLY BY 500(10).
1293   16426  6575           (0764)
1294   16427  7407           DVI              /AND DIVIDE BY SDAUTO.
1295   16430  6436           PQAS2
1296   16431  7521           SWP              /PUT THE RESULT IN THE AC.
1297   16432  7430           SZL              /TEST FOR DIVIDE OVERFLOW.
1298   16433  2144           ISZ PQABAD       /DID OVERFLOW, SAY REJECT THE SHEET
1299
1300   16434  1237           TAD PQAS3        /NOW WE CAN ADD IN THE ORIGINAL SDP
1301   16435  5607           JMP I PQAS1      /AND WE'RE ALL DONE, RETURN.

/ PRODUCT QUALITY ALGORITHM                  PAL8-V10A 08/08/77  PAGE 50

1302                  /
1303   16436  0000    PQAS2, 0                /TEMPORARIES FOR PQASDN
1304   16437  0000    PQAS3, 0
1305
1306   16575  0764
1307   16576  6321
1308   16577  0070
1309          6600            PAGE

/ PRODUCT QUALITY ALGORITHM                  PAL8-V10A 08/08/77  PAGE 51

1310                  /
1311                  /
1312                  /
1313                  /       DATA TABLES FOR THE ALGORITHM - IN DECIMAL RADIX
1314                  /
1315                  /
1316                                          /*****
1317                                          /*****
1318                          DECIMAL         /*****
1319                                          /*****
1320                                          /*****
1321                  /
1322                  /
1323                  /       TABLE OF NORMALIZED FEATURE DATA VALUES
1324                  /
1325                  /
1326   16600  0000    RAWDAT, 0                /FEATURE 1.
1327   16601  0000            0
1328   16602  0000            0
1329   16603  0000            0
1330   16604  0000            0
1331   16605  0000            0                /FEATURE 6
1332   16606  0000            0
1333   16607  0000            0
1334                  /
1335                  /
```

```
1336                    /         TABLE OF NORMALIZED FEATURE DATA
1337                    /
1338                    /
1339   16610  0000  NORMDT,  0              /FEATURE 1
1340   16611  0000           0
1341   16612  0000           0
1342   16613  0000           0
1343   16614  0000           0
1344   16615  0000           0              /FEATURE 6
1345   16616  0000           0
1346   16617  0000           0
1347                    /
1348                    /
1349                    /         TABLE OF COMPUTED DISTANCE VECTORS
1350                    /
1351                    /
1352   16620  0000  VECTBL,  0              /VECTOR 1
1353   16621  0000           0
1354   16622  0000           0
1355   16623  0000           0
1356   16624  0000           0
1357   16625  0000           0              /VECTOR 6
1358   16626  0000           0
1359   16627  0000           0
```

/ PRODUCT QUALITY ALGORITHM                PAL8-V10A 08/08/77  PAGE 52

```
1360                    /
1361                    /
1362                    /
1363                    /         TABLE OF FEATURE MEANS - CHANNEL 1
1364                    /
1365                    /
1366   16630  0310  MEN1,    200            /CH2 SDPK
1367   16631  0006           6              /CH1 TOTPA
1368   16632  0004           4              /CH1 TOTNA
1369   16633  0505           325            /CH1 SDPK
1370   16634  0005           5              /CH1 XDMIN
1371   16635  0002           2              /CH1 MDMIN
1372                    /
1373                    /
1374                    /         TABLE OF STANDARD DEVIATIONS - CHANNEL 1
1375                    /
1376                    /
1377   16636  0144  STD1,    100            /CH2 SDPK
1378   16637  0016           14             /CH1 TOTPA
1379   16640  0010           8              /CH1 TOTNA
1380   16641  0113           75             /CH1 SDPK
1381   16642  0007           7              /CH1 XDMAX
1382   16643  0003           3              /CH1 MDMAX
1383                    /
1384                    /
1385                    /
1386                    /         TABLE OF FEATURE MEANS - CHANNEL 3
1387                    /
1388                    /
1389   16644  0310  MEN3,    200            /CH2 SDPK
1390   16645  0006           6              /CH3 TOTPA
1391   16646  0004           4              /CH3 TOTNA
1392   16647  0505           325            /CH3 SDPK
1393   16650  0005           5              /CH3 XDMIN
1394   16651  0002           2              /CH3 MDMIN
```

```
1395                /
1396                /
1397                /       TABLE OF STANDARD DEVIATIONS - CHANNEL 3
1398                /
1399                /
1400   16652  0144  STD3,  100         /CH2 SDPK
1401   16653  0016         14          /CH3 TOTPA
1402   16654  0010         8           /CH3 TOTNA
1403   16655  0113         75          /CH3 SDPK
1404   16656  0007         7           /CH3 XDMAX
1405   16657  0003         3           /CH3 MDMAX
```

/ PRODUCT QUALITY ALGORITHM                    PAL8-V10A 08/08/77   PAGE 53

```
1406                /
1407                /
1408                /
1409                /       TABLE OF DISTANCE VECTOR FACTORS - CHANNEL 1
1410                /
1411                /       TABLE FORMAT IS:   G(I,J), I=1,6, J=1,6
1412                /
1413                /       STORED BY VECTOR:  G(1,1), G(1,2), ..., G(1,6)
1414                /                          G(2,1), G(2,2), ..., G(2,6)
1415                /                             .       .           .
1416                /                             .       .           .
1417                /                          G(6,1), G(6,2), ..., G(6,6)
1418                /
1419                /
1420   16660  7734  FAC1,  -36         /CH2 SDPK        VECTOR 1 (GOOD)
1421   16661  7771         -7          /CH1 TOTPA
1422   16662  7750         -24         /CH1 TOTNA
1423   16663  7773         -5          /CH1 SDPK
1424   16664  7760         -16         /CH1 XDMAX
1425   16665  0006         6           /CH1 MDMAX
1426
1427   16666  7730         -40         /CH2 SDPK        VECTOR 2 (GOOD)
1428   16667  7753         -21         /CH1 TOTPA
1429   16670  0030         24          /CH1 TOTNA
1430   16671  7760         -16         /CH1 SDPK
1431   16672  0013         11          /CH1 XDMAX
1432   16673  0006         6           /CH1 MDMAX
1433
1434   16674  7731         -39         /CH2 SDPK        VECTOR 3 (GOOD)
1435   16675  7753         -21         /CH1 TOTPA
1436   16676  7720         -48         /CH1 TOTNA
1437   16677  7771         -7          /CH1 SDPK
1438   16700  7742         -30         /CH1 XDMAX
1439   16701  7742         -30         /CH1 MDMAX
1440
1441   16702  0247         167         /CH2 SDPK        VECTOR 4 (BAD)
1442   16703  0072         58          /CH1 TOTPA
1443   16704  0170         120         /CH1 TOTNA
1444   16705  0164         116         /CH1 SDPK
1445   16706  0103         67          /CH1 XDMAX
1446   16707  0052         42          /CH1 MDMAX
1447
```

```
1448  16710  7732        -38       /CH2 SDPK     VECTOR 5 (BAD)
1449  16711  0026         22       /CH1 TOTPA
1450  16712  0140         96       /CH1 TOTNA
1451  16713  0047         39       /CH1 SDPK
1452  16714  0137         95       /CH1 XDMAX
1453  16715  0006          6       /CH1 MDMAX
1454
1455  16716  0007          7       /CH2 SDPK     VECTOR 6 (BAD)
1456  16717  0010          8       /CH1 TOTPA
1457  16720  0030         24       /CH1 TOTNA
1458  16721  0014         12       /CH1 SDPK
1459  16722  0031         25       /CH1 XDMAX
1460  16723  0006          6       /CH1 MDMAX
```

/ PRODUCT QUALITY ALGORITHM                    PAL8-V10A 08/08/77  PAGE 54

```
1461                    /
1462                    /
1463                    /
1464                    /   TABLE OF DISTANCE VECTOR FACTORS - CHANNEL 3
1465                    /
1466                    /   TABLE FORMAT IS:   G(I,J), I=1,6, J=1,6
1467                    /
1468                    /   STORED BY VECTOR:  G(1,1), G(1,2), ..., G(1,6)
1469                    /                      G(2,1), G(2,2), ..., G(2,6)
1470                    /                         .       .           .
1471                    /                         .       .           .
1472                    /                      G(6,1), G(6,2), ..., G(6,6)
1473                    /
1474                    /
1475  16724  7734  FAC3, -36       /CH2 SDPK     VECTOR 1 (GOOD)
1476  16725  7771        -7        /CH3 TOTPA
1477  16726  7750        -24       /CH3 TOTNA
1478  16727  7773        -5        /CH3 SDPK
1479  16730  7760        -16       /CH3 XDMAX
1480  16731  0006         6        /CH3 MDMAX
1481
1482  16732  7730        -40       /CH2 SDPK     VECTOR 2 (GOOD)
1483  16733  7753        -21       /CH3 TOTPA
1484  16734  0030         24       /CH3 TOTNA
1485  16735  7760        -16       /CH3 SDPK
1486  16736  0013         11       /CH3 XDMAX
1487  16737  0006          6       /CH3 MDMAX
1488
1489  16740  7731        -39       /CH2 SDPK     VECTOR 3 (GOOD)
1490  16741  7753        -21       /CH3 TOTPA
1491  16742  7720        -48       /CH3 TOTNA
1492  16743  7771        -7        /CH3 SDPK
1493  16744  7742        -30       /CH3 XDMAX
1494  16745  7742        -30       /CH1 MDMAX
1495
1496  16746  0247        167       /CH2 SDPK     VECTOR 4 (BAD)
1497  16747  0072         58       /CH3 TOTPA
1498  16750  0170        120       /CH3 TOTNA
1499  16751  0164        116       /CH3 SDPK
1500  16752  0103         67       /CH3 XDMAX
1501  16753  0052         42       /CH3 MDMAX
1502
```

| | | | | | |
|---|---|---|---|---|---|
|1503|16754|7732|-38|/CH2 SDPK|VECTOR 5 (BAD)|
|1504|16755|0026|22|/CH3 TOTPA| |
|1505|16756|0140|96|/CH3 TOTNA| |
|1506|16757|0047|39|/CH3 SDPK| |
|1507|16760|0137|95|/CH3 XDMAX| |
|1508|16761|0006|6|/CH3 MDMAX| |
|1509| | | | | |
|1510|16762|0007|7|/CH2 SDPK|VECTOR 6 (BAD)|
|1511|16763|0010|8|/CH3 TOTPA| |
|1512|16764|0030|24|/CH3 TOTNA| |
|1513|16765|0014|12|/CH3 SDPK| |
|1514|16766|0031|25|/CH3 XDMAX| |
|1515|16767|0006|6|/CH3 MDMAX| |

/ PRODUCT QUALITY ALGORITHM                          PAL8-V10A 08/08/77    PAGE 55

```
1516                    /
1517
1518            7000        PAGE
1519
1520                    $=$=LHN=$=$
```

/ PRODUCT QUALITY ALGORITHM                          PAL8-V10A 08/08/77    PAGE 56

| | | | | | | | | |
|---|---|---|---|---|---|---|---|---|
|ACL|7721|BUF2AD|7000|DBSK|6002|LSTFLG|0001| |
|ACS|7403|CAL|4020|DBSO|6006|MARKTI|0000| |
|AC0001|7301|CALODT|4033|DB8FLD|0010|MAXDEX|6243| |
|AC0002|7326|CAM|7621|DB8LOC|0200|MAXVAL|6242| |
|AC2000|7332|CANCEL|7000|DB8PGZ|0100|MCR|0047| |
|AC3777|7350|CDI|6203|DCM|7575|MCRDV|0035| |
|AC4000|7330|CHECKP|0000|DEBUG|0015|MCRCLK|0001| |
|AC5777|7352|CHECKW|0037|DEBWT|0004|MCRDMP|0001| |
|AC7775|7346|CHL1|4470|DECODE|0010|MCREF|0070| |
|AC7776|7344|CHL12|4503|DERAIL|0037|MCRFLD|0030| |
|AC7777|7340|CHL123|4516|DLD|7663|MCRLOC|0200| |
|AIR0|0010|CHL13|4510|DNEWT|0001|MCRPGZ|0150| |
|AIR1|0011|CHL2|4472|DPIC|7573|MCRSYS|0001| |
|AIR2|0012|CHL23|4513|DPSZ|7451|MCR6CN|0001| |
|AIR3|0013|CHL3|4506|DR8|0003|MDMAX|0032| |
|AIR4|0014|CH1BAS|0067|DR8FLD|0010|MD1|0010| |
|AIR5|0015|CH1DAT|0004|DR8LOC|1200|MD2|0011| |
|AIR6|0016|CH1EFG|0060|DR8SI|0510|MEMDAT|0046| |
|AIR7|0017|CH1IST|0140|DST|7445|MEN1|6630| |
|ALGO|0013|CH1OFL|0063|DUMP|0043|MEN3|6644| |
|ALGOFL|0010|CH2BAS|0070|DVI|7407|MINDEX|6307| |
|ALGOLD|4400|CH2DAT|0005|EAE|0001|MINVAL|6306| |
|ALGOPG|0140|CH2EFG|0061|EFPKN|0036|MIS1FL|0020| |
|ALGOTL|4460|CH2IST|0141|EFPKP|0035|MIS1LO|0200| |
|ALG1|4522|CH2OFL|0064|EFWT|2000|MOVDAT|6340| |
|ALG10|4532|CH3BAS|0071|EMULFT|0015|MOVD1|6342| |
|ALG11|4552|CH3DAT|0006|ENABWT|0040|MQ|0001| |
|ALG12|4553|CH3EFG|0062|ENDATC|0052|MSBW1|0017| |
|ALNUA|6160|CH3IST|0142|EORMWT|0200|MSBW2|0021| |
|ALNUMD|6133|CH3LOC|0041|FAC1|6660|MSGTBL|1376| |
|ALN1|6157|CH3OFL|0065|FAC3|6724|MSGWT|0020| |
|AL1|4600|CLB|7300|FCLOSE|0017|MUY|7405| |
|AL1A|4701|CLKQLN|0020|FIMQDY|0074|NETWT|0010| |
|AL1B|4722|CLKTYP|0000|FREE|4000|NEWROL|0020| |
|AL1C|4723|CLOCK|0001|GETDAT|6321|NIAT|0024| |

| | | | | | | | |
|---|---|---|---|---|---|---|---|
| AL1F | 5000 | COMMAN | 0050 | HERTZ | 0170 | NMI | 7411 |
| AL1G | 5023 | COMMST | 0027 | HGHFLD | 0070 | NOCRLF | 2000 |
| AL1XIT | 4660 | CONDAT | 0054 | IND | 1000 | NOLINE | 0400 |
| AL2 | 5200 | CUR | 0010 | INITZE | 0045 | NONRWT | 4000 |
| AL2A | 5234 | CURSAM | 0044 | INIWT | 0000 | NOPACK | 4000 |
| AL2B | 5246 | DAD | 7443 | INIWT2 | 0000 | NORMDT | 6610 |
| AL2F | 5274 | DATBAS | 2000 | INIWT3 | 0000 | NSDPK | 0145 |
| AL3 | 5400 | DATCFL | 0010 | INIWT4 | 0000 | NSDPK2 | 0146 |
| AL3A | 5501 | DATCLO | 1400 | ISTATU | 0012 | NTASKS | 0050 |
| AL3B | 5522 | DATCPG | 0110 | KBDEV | 0003 | NULL | 0051 |
| AL3C | 5523 | DATDEV | 0011 | KLBA | 0000 | NULLFL | 0000 |
| AL3F | 5600 | DATE | 0047 | KLBALI | 0100 | NULLLO | 3500 |
| AL3G | 5623 | DATFLD | 0020 | LASTQL | 0072 | NUMDEF | 0013 |
| AL3XIT | 5460 | DATLEN | 4000 | LDPKN | 0027 | ODTBKF | 0072 |
| ASR | 7415 | DBCI | 6003 | LDPKP | 0026 | OS8F | 0016 |
| ASSGN | 0200 | DBCO | 6005 | LOGNAM | 0041 | OS8FFL | 0000 |
| BLKARG | 0010 | DBDI | 6000 | LPT | 0046 | OS8FLO | 6200 |
| BUFFLD | 0020 | DBEI | 6001 | LPTFLD | 0030 | OS8FPG | 0160 |
| BUFLEN | 1000 | DBRI | 6004 | LPTLOC | 3200 | OS8HPR | 0071 |
| BUF1AD | 6002 | DBRO | 6007 | LSR | 7417 | OWNTTY | 0073 |

/ PRODUCT QUALITY ALGORITHM                              PAL8-V10A 08/08/77   PAGE 56-1

| | | | | | |
|---|---|---|---|---|---|
| PARTNS | 0000 | QUALFL | 0010 | TALFLD | 0040 |
| POP12 | 0000 | QUALLO | 3600 | TALK | 0037 |
| POP8A | 0000 | QUALPG | 0130 | TALLY | 0033 |
| POP8E | 0001 | RAWDAT | 6600 | TALPTR | 0047 |
| PERIOD | 2000 | RECEIV | 0001 | TALSUM | 0032 |
| PIAT | 0023 | RESCHD | 0013 | TASK | 0013 |
| PLDMDN | 0005 | RK8E | 0011 | TFTABL | 2036 |
| PLDMDP | 0003 | RK8EFL | 0003 | TIMOUT | 2000 |
| PLDXDN | 0004 | RK8ELO | 3200 | TLYFLD | 0040 |
| PLDXDP | 0002 | ROLLIN | 0040 | TLYLOC | 0200 |
| POST | 0005 | RUN | 0003 | TODH | 0046 |
| POSTDS | 5424 | RUNWT | 1000 | TODL | 0045 |
| PQABAD | 0144 | SAM | 7457 | TOTNA | 0020 |
| PQAMAA | 6240 | SAMLOC | 0045 | TOTPA | 0016 |
| PQAMAB | 6241 | SAMNUM | 0043 | TRY | 0044 |
| PQAMAX | 6200 | SAMPFL | 0010 | TSTABL | 1515 |
| PQAMA1 | 6220 | SAMPLE | 0021 | TSWFLG | 0044 |
| PQAMA2 | 6234 | SAMPLO | 2400 | TTDEV | 0004 |
| PQAMIA | 6304 | SAMREC | 0042 | TTY | 0035 |
| PQAMIB | 6305 | SCA | 7441 | TTYFLD | 0000 |
| PQAMIN | 6244 | SCHEDU | 1000 | TTYLOC | 3600 |
| PQAMI1 | 6264 | SCL | 7403 | TTYST | 0025 |
| PQAMI2 | 6300 | SDAUTO | 0022 | TTYSTF | 0020 |
| PQANA | 6063 | SDPK | 0025 | TTYSTL | 0600 |
| PQANB | 6064 | SELDAT | 0053 | UNBARG | 0012 |
| PQAN1 | 6020 | SELFCK | 0037 | USRRWT | 0100 |
| PQAN2 | 6036 | SELFFL | 0030 | VECTBL | 6620 |
| PQAN3 | 6060 | SELFLO | 4000 | VERS | 0001 |
| PQASCR | 0143 | SELFPG | 0100 | VERS2 | 0000 |
| PQASDN | 6400 | SEND | 0000 | VERS3 | 0000 |
| PQAS1 | 6407 | SENDW | 0011 | VERS4 | 0000 |
| PQAS2 | 6436 | SHDONE | 0056 | WAITE | 0002 |
| PQAS3 | 6437 | SHERTZ | 0170 | WAITM | 4425 |
| PQATST | 6310 | SHL | 7413 | WAITX | 0014 |
| PQAVA | 6131 | SHSTAT | 0057 | XDMAX | 0031 |
| PQAVB | 6132 | SHTCNT | 0051 | XD1 | 0006 |
| PQAVEC | 6065 | SHUTDP | 0066 | XD2 | 0007 |
| PQAV1 | 6100 | SISROL | 0050 | ZERO | 0030 |
| PQAV2 | 6105 | SKB | 7471 | | |
| PQAV3 | 6122 | SKPINS | 6006 | | |

```
PQAV4    6127       SNAP    0042
PQIVER   6504       SNAPFL  0020
PUNORM   6000       SNAPLO  1200
PQRS     0014       START   4400
PQRSCD   0055       STD1    6636
PSDMD    0001       STD3    6652
PSDXD    0000       STK1    0014
PUTDAT   6331       STK2    0030
PWRCLR   3200       STPKN   0034
PWRF     0002       STPKP   0033
PWRFAL   0001       SUSPND  0004
PWRFFL   0000       SWAB    7431
PWRFLO   3000       SWBA    7447
QFIN     0015       SWPWT   0400
QUAL     0012       TALBUF  1000

ERRORS DETECTED: 0
LINKS GENERATED: 64
```

| | | | | | | | | |
|---|---|---|---|---|---|---|---|---|
| ACL    | 524   | 563   | 568   | 587  | 820  | 894  | 901  |      |
| AIR5   | 370   | 375   | 665   | 670  | 860  | 874  | 948  | 963  | 1244 |
| AIR6   | 872   | 904   | 957   | 965  |      |      |      |      |
| AIR7   | 954   | 980   |       |      |      |      |      |      |
| ALGO   | 34    |       |       |      |      |      |      |      |
| ALGOFL | 35    |       |       |      |      |      |      |      |
| ALGOLO | 52    |       |       |      |      |      |      |      |
| ALGOPG | 41    |       |       |      |      |      |      |      |
| ALGOTL | 217   | 228#  |       |      |      |      |      |      |
| ALG1   | 242   | 257   | 260   | 264  | 268  | 273  | 280# |      |
| ALG10  | 207   | 250   | 294#  |      |      |      |      |      |
| ALG11  | 228   | 253   | 285   | 296  | 319# |      |      |      |
| ALG12  | 307   | 311   | 322#  |      |      |      |      |      |
| ALNUA  | 1017  | 1022  | 1023  | 1029 | 1039#|      |      |      |
| ALNUMD | 358   | 548   | 653   | 1012#| 1031 | 1032 | 1035 | 1037 |
| ALN1   | 1037# |       |       |      |      |      |      |      |
| AL1    | 241   | 255   | 262   | 270  | 348# | 429  | 472  |      |
| AL1A   | 438   | 451#  |       |      |      |      |      |      |
| AL1B   | 449   | 454   | 471#  |      |      |      |      |      |
| AL1C   | 443   | 448   | 461   | 466  | 472# |      |      |      |
| AL1F   | 353   | 504#  |       |      |      |      |      |      |
| AL1G   | 360   | 507   | 527#  |      |      |      |      |      |
| AL1XIT | 429#  | 514   | 528   |      |      |      |      |      |
| AL2    | 244   | 256   | 266   | 271  | 541# | 580  | 622  | 625  |
| AL2A   | 566   | 587#  |       |      |      |      |      |      |
| AL2B   | 599#  |       |       |      |      |      |      |      |
| AL2F   | 546   | 550   | 571   | 578  | 590  | 597  | 616  | 621  | 624# |
| AL3    | 259   | 263   | 267   | 272  | 643# | 725  | 768  |      |
| AL3A   | 734   | 747#  |       |      |      |      |      |      |
| AL3B   | 745   | 750   | 767#  |      |      |      |      |      |
| AL3C   | 739   | 744   | 757   | 762  | 768# |      |      |      |
| AL3F   | 648   | 800#  |       |      |      |      |      |      |
| AL3G   | 655   | 803   | 823#  |      |      |      |      |      |
| AL3XIT | 725#  | 810   | 824   |      |      |      |      |      |
| CAL    | 152   | 314   | 324   |      |      |      |      |      |
| CAM    | 892   |       |       |      |      |      |      |      |
| CHECKW | 97#   |       |       |      |      |      |      |      |

| Symbol | | | | | | | | | | |
|---|---|---|---|---|---|---|---|---|---|---|
| CHL1 | 229 | 241# | | | | | | | | |
| CHL12 | 231 | 255# | | | | | | | | |
| CHL123 | 235 | 270# | | | | | | | | |
| CHL13 | 233 | 262# | | | | | | | | |
| CHL2 | 230 | 244# | | | | | | | | |
| CHL23 | 234 | 266# | | | | | | | | |
| CHL3 | 232 | 259# | | | | | | | | |
| CH1BAS | 162 | 377 | 431 | 434 | 456 | 510 | 517 | 1014 | | |
| CH1IST | 43# | 165 | 166 | 191 | 350 | 504 | | | | |
| CH2BAS | 171 | 372 | 559 | 573 | 592 | 599 | 603 | 667 | 1019 | 1270 |
| CH2IST | 44# | 174 | 175 | 193 | 543 | | | | | |
| CH3BAS | 181 | 672 | 727 | 730 | 752 | 806 | 813 | 1025 | | |
| CH3IST | 45# | 184 | 185 | 196 | 645 | 800 | | | | |
| CLB | 151 | 159 | 168 | 177 | 187 | 280 | 304 | 322 | 349 | 388 |
|  | 542 | 644 | 683 | 857 | 912 | 945 | 974 | 1013 | 1067 | 1070 |
|  | 1126 | 1129 | 1180 | 1217 | | | | | | |
| CUR | 10 | 10 | 35# | 39 | 1204 | 1216 | | | | |
| DATFLD | 1202 | 1214 | | | | | | | | |
| DVI | 522 | 612 | 818 | 889 | 1294 | | | | | |
| EFPKN | 96# | | | | | | | | | |
| EFPKP | 95# | | | | | | | | | |
| EMULFT | 77# | | | | | | | | | |
| FAC1 | 407 | 1420# | | | | | | | | |
| FAC3 | 702 | 1475# | | | | | | | | |
| GETDAT | 163 | 172 | 182 | 373 | 435 | 457 | 511 | 518 | 560 | 574 |
|  | 593 | 600 | 604 | 668 | 731 | 753 | 807 | 814 | 1015 | 1020 |
|  | 1026 | 1198# | 1199 | 1200 | 1201 | 1203 | 1205 | 1215 | 1242 | 1279 |
|  | 1283 | | | | | | | | | |
| INIWT | 16 | 36# | | | | | | | | |
| ISTATU | 74# | 164 | 173 | 183 | | | | | | |
| LASTQL | 249 | 288 | 319 | | | | | | | |
| LDPKN | 88# | | | | | | | | | |
| LDPKP | 87# | | | | | | | | | |
| MAXDEX | 1077 | 1080 | 1097 | 1107# | | | | | | |
| MAXVAL | 1083 | 1086 | 1093 | 1106# | 1181 | | | | | |
| MDMAX | 92# | 383 | 519 | 575 | 594 | 678 | 815 | | | |
| MD1 | 72# | | | | | | | | | |
| MD2 | 73# | | | | | | | | | |
| MEN1 | 400 | 1366# | | | | | | | | |
| MEN3 | 695 | 1389# | | | | | | | | |
| MINDEX | 1136 | 1139 | 1156 | 1166# | | | | | | |
| MINVAL | 1142 | 1145 | 1152 | 1165# | 1183 | | | | | |
| MOVDAT | 378 | 673 | 1234# | 1235 | 1236 | 1237 | 1239 | 1241 | | |
| MOVD1 | 1236# | 1245 | | | | | | | | |
| MSBW1 | 79# | | | | | | | | | |
| MSBW2 | 82# | | | | | | | | | |
| MSGTBL | 7 | | | | | | | | | |
| MUY | 610 | 887 | 1292 | | | | | | | |
| NIAT | 85# | | | | | | | | | |
| NORMDT | 871 | 956 | 1339# | | | | | | | |
| NSDPK | 48# | 440 | 463 | 736 | 759 | 1269 | | | | |
| NSDPK2 | 49# | 445 | 451 | 468 | 741 | 747 | 764 | 1272 | | |
| NUMDEF | 75# | 512 | 808 | 1016 | 1021 | 1027 | | | | |
| PIAT | 84# | | | | | | | | | |
| PLDMDN | 68# | | | | | | | | | |
| PLDMDP | 66# | | | | | | | | | |
| PLDXDN | 67# | | | | | | | | | |
| PLDXDP | 65# | | | | | | | | | |
| PQABAD | 47# | 213 | 245 | 281 | 392 | 395 | 427 | 471 | 527 | 608 |
|  | 624 | 687 | 690 | 723 | 767 | 823 | 913 | 975 | 1185 | 1290 |
|  | 1298 | | | | | | | | | |

| | | | | | | | | | |
|---|---|---|---|---|---|---|---|---|---|
| PQAMAA | 1081 | 1082 | 1085 | 1088 | 1092 | 1104# | | | |
| PQAMAB | 1069 | 1095 | 1105# | | | | | | |
| PQAMAX | 413 | 708 | 1066# | 1068 | 1071 | 1072 | 1076 | 1096 | 1101 | 1102 |
| PQAMA1 | 1085# | 1100 | | | | | | | |
| PQAMA2 | 1090 | 1099# | | | | | | | |
| PQAMIA | 1140 | 1141 | 1144 | 1147 | 1151 | 1163# | | | |
| PQAMIB | 1128 | 1154 | 1164# | | | | | | |
| PQAMIN | 419 | 714 | 1125# | 1127 | 1130 | 1131 | 1135 | 1155 | 1160 | 1161 |
| PQAMI1 | 1144# | 1159 | | | | | | | |
| PQAMI2 | 1149 | 1158# | | | | | | | |
| PQANA | 870 | 876 | 883 | 906 | 917# | | | | |
| PQANB | 877 | 878 | 899 | 918# | | | | | |
| PQAN1 | 874# | 909 | | | | | | | |
| PQAN2 | 863 | 890# | 907 | | | | | | |
| PQAN3 | 885 | 897 | 912# | | | | | | |
| PQASCR | 46# | 169 | 178 | 179 | 188 | 189 | 216 | 515 | 523 | 602 |
| | 613 | 617 | 811 | 819 | 868 | 908 | 960 | 978 | 1074 | 1094 |
| | 1099 | 1133 | 1153 | 1158 | 1276 | 1278 | 1282 | | | |
| PQASDN | 432 | 728 | 1267# | 1273 | | | | | | |
| PQAS1 | 1268 | 1271 | 1275# | 1301 | | | | | | |
| PQAS2 | 1281 | 1295 | 1303# | | | | | | |
| PQAS3 | 1286 | 1287 | 1300 | 1304# | | | | | |
| PQATST | 425 | 721 | 1179# | 1186 | | | | | |
| PQAVA | 962 | 969 | 987# | | | | | | |
| PQAVB | 952 | 981 | 988# | | | | | | |
| PQAVEC | 406 | 701 | 944# | 946 | 947 | 949 | 950 | 958 | 983 | 984 |
| PQAV1 | 956# | 982 | | | | | | | |
| PQAV2 | 962# | 979 | | | | | | | |
| PQAV3 | 972 | 978# | | | | | | | |
| PQAV4 | 976 | 983# | | | | | | | |
| PQNORM | 399 | 694 | 856# | 858 | 859 | 861 | 862 | 865 | 866 | 910 |
| | 914 | | | | | | | | |
| PQRS | 313 | | | | | | | | |
| PQRSCD | 204 | 305 | | | | | | | |
| PSDMD | 64# | | | | | | | | |
| PSDXD | 63# | | | | | | | | |
| PUTDAT | 1213# | 1218 | | | | | | | |
| QFIN | 323 | | | | | | | | |
| RAWDAT | 369 | 389 | 390 | 664 | 684 | 685 | 869 | 1326# | | |
| RUN | 315 | 325 | | | | | | | |
| SDAUTO | 83# | 601 | 1280 | | | | | | |
| SDPK | 86# | 374 | 381 | 605 | 669 | 676 | 1284 | | |
| SHSTAT | 198 | 294 | | | | | | | |
| START | 11 | 151# | 316 | 326 | | | | | |
| STD1 | 401 | 1377# | | | | | | | |
| STD3 | 696 | 1400# | | | | | | | |
| STK1 | 76# | | | | | | | | |
| STK2 | 90# | | | | | | | | |
| STPKN | 94# | | | | | | | | |
| STPKP | 93# | | | | | | | | |
| SUSPND | 153 | | | | | | | | |
| SWAB | 160 | | | | | | | | |
| TASK | 7 | 9 | 15 | 34# | | | | | |
| TFTABL | 15 | | | | | | | | |
| TOTNA | 81# | 380 | 675 | | | | | | |
| TOTPA | 78# | 379 | 674 | | | | | | |
| TSTABL | 9 | | | | | | | | |
| VECTBL | 953 | 1079 | 1138 | 1352# | | | | | |
| VERS | 13 | 19# | | | | | | | |
| XDMAX | 91# | 382 | 436 | 458 | 561 | 677 | 732 | 754 | |
| XD1 | 69# | | | | | | | | |

| X02 | 70# | |
|---|---|---|
| 014564 | 323 | |
| 014565 | 313 | |
| 014566 | 287 | |
| 014567 | 284 | |
| 014571 | 252 | |
| 014572 | 248 | |
| 014575 | 217 | |
| 014576 | 205 | 309 |
| 014752 | 469 | |
| 014753 | 464 | |
| 014754 | 459 | |
| 014755 | 446 | 452 |
| 014756 | 441 | |
| 014760 | 431 | |
| 014766 | 393 | |
| 014773 | 369 | |
| 014777 | 351 | |
| 015174 | 525 | |
| 015177 | 505 | |
| 015367 | 619 | |
| 015370 | 611 | |
| 015371 | 588 | |
| 015372 | 576 | |
| 015373 | 569 | |
| 015374 | 564 | |
| 015377 | 544 | |
| 015552 | 765 | |
| 015553 | 760 | |
| 015554 | 755 | |
| 015555 | 742 | 748 |
| 015556 | 737 | |
| 015560 | 727 | |
| 015566 | 688 | |
| 015573 | 664 | |
| 015577 | 646 | |
| 015774 | 821 | |
| 015777 | 801 | |
| 016173 | 953 | |
| 016174 | 895 | |
| 016175 | 888 | |
| 016176 | 871 | 956 |
| 016177 | 869 | |
| 016377 | 1079 | 1138 |
| 016575 | 1293 | |
| 016577 | 1270 | |
| V4 | | |

We claim:

1. A method of automatically inspecting, by a sequence of areas of preselected size, a running web for defects using a flying spot scanning system, by repetitively measuring a plurality of web features which may contribute to a web defect, each feature represented by an electrical signal extracted in the course of scanning said web, and analyzing said extracted feature signals with regard to each said area of preselected size comprising of steps of:
    converting said plurality of extracted feature signals, obtained from scanning each area, into a set of area characterizing feature values representative of the magnitudes and distribution of said extracted features over each said scanned area;
    calibrating each said set of area characterizing feature values to obtain correspondence with a range of stored values specifying one or more sets of reference feature values;
    classifying each said set of calibrated area characterizing feature values according to its relationship with said one or more sets of reference feature values; and
    grading as to acceptability each defective web area in said inspected sequence of areas based on the outcome of said classification.

2. The method of claim 1 wherein said step of calibrating each step of area characterizing feature values, comprises:
    identifying the occurrence of any gross defects in the scanned area for immediate grading of said area as non-acceptable;
    compensating said characterizing feature values for differences in interchannel scan geometries; and
    scaling the largest peak amplitude detected in each scanned area with respect to the amplitude of a calibration signal occurring during the scansion at the location of said largest peak amplitude.

3. The method of claim 2 wherein said reference feature values are derived by collecting calibrated area characterizing feature data on-line from said reference web, comparing off-line said collected data with known visual quality standards corresponding to said scanned sequence of areas, and using the results of said comparison to refine said set of calibrated area characterizing feature values.

4. The method of claim 2 wherein said step of calibrating each said set of area characterizing feature values comprises normalizing those feature values relating to area, duration and peak amplitude with respect to the mean and standard deviation of the corresponding reference feature values derived from measurements of a reference web.

5. A flying spot scan automatic on-line inspection system for a running web for detecting defects in a sequence of areas of preselected size associated with said web by repetitively measuring a plurality of web features represented by a first set of electrical signals extracted in the course of scanning said web and analyzing said first set of feature electrical signals with regard to each said scanned area of preselected size, comprising:
    means for converting said first set of electrical signals into a second set of electrical signals representative of the magnitudes and distribution of said plurality of repetitively measured features over each said scanned area;
    means for calibrating each said second set of second electrical signals to obtain calibrated signals that correspond with the ranges of values specifying one or more sets of reference feature values;
    means for classifying each said set of calibrated signals according to its relationship with said one or more sets of stored reference feature values; and
    means based on the outcome of said classification for grading said classified calibrated signals for each said area in said inspected sequence of areas as to acceptability.

6. A flying spot scan automatic on-line inspection system for a running web according to claim 5 wherein said web is x-ray film.

7. The system of claim 5 wherein said means for converting includes a feature extractor for selectively acquiring predetermined scan signal features, and a feature processor for converting said predetermined scan signal features for each said scanned area, thereby permitting product grading on a real time basis.

* * * * *